United States Patent [19]

Bendiak

[11] Patent Number: 5,403,927
[45] Date of Patent: Apr. 4, 1995

[54] SEQUENTIAL REMOVAL OF MONOSACCHARIDES FROM THE REDUCING END OF OLIGOSACCHARIDES AND USES THEREOF

[75] Inventor: Brad K. Bendiak, Seattle, Wash.

[73] Assignee: The Biomembrane Institute, Seattle, Wash.

[21] Appl. No.: 134,101

[22] Filed: Oct. 7, 1993

Related U.S. Application Data

[63] Continuation-in-part of Ser. No. 891,580, Jun. 1, 1992, abandoned.

[51] Int. Cl.$^6$ .................. C07H 5/06; C07H 17/00; A61K 31/70; C08B 37/00
[52] U.S. Cl. .................................................... 536/124
[58] Field of Search ......................................... 536/124

[56] References Cited

U.S. PATENT DOCUMENTS

| | | | |
|---|---|---|---|
| 4,587,331 | 5/1986 | Hlavka et al. | 536/18.7 |
| 4,721,781 | 1/1988 | Rowton | 536/124 |
| 4,831,128 | 5/1989 | Tsai et al. | 536/124 |
| 4,868,289 | 9/1989 | Magnusson et al. | 536/18.4 |
| 4,912,094 | 3/1990 | Myers et al. | 536/124 |
| 4,918,009 | 4/1990 | Nilsson | 536/17.4 |
| 4,943,630 | 7/1990 | Jacquinet et al. | 536/124 |
| 4,992,536 | 2/1991 | Bilmers et al. | 536/120 |
| 5,142,031 | 8/1992 | Lee et al. | 536/124 |

OTHER PUBLICATIONS

Bendiak et al., *Glycobiology*, vol. 2, No. 5, p. 460, item 1.14 (1992) (21st Annual Meeting of the Society for Complex Carbohydrates, Nashville, Tenn., Nov. 11–14, 1992.

*Primary Examiner*—Ronald W. Griffin
*Attorney, Agent, or Firm*—Seed and Berry

[57] ABSTRACT

Methods are provided for the sequential removal of monosaccharides from the reducing end of oligosaccharides. The present invention also discloses the use of such methods for structural determinations of oligosaccharides and to enable new structures to be generated from pre-existing oligosaccharides. In addition, the methods of the present invention may be automated by the incorporation into systems.

14 Claims, 2 Drawing Sheets

1. Ruff or Whistler-Schweiger degradation

2. Cleavage

3. Deprotection

SEQUENTIAL REMOVAL OF MONOSACCHARIDES FROM THE REDUCING END OF OLIGOSACCHARIDES AND USES THEREOF

CROSS REFERENCE TO RELATED APPLICATION

This application is a continuation-in-part application to Ser. No. 07/891,580, filed Jun. 1, 1992, now abandoned.

TECHNICAL FIELD

The present invention relates generally to the sequential removal of monosaccharides from oligosaccharides. This invention is more particularly related to methods for the sequential removal of monosaccharides from the reducing end of oligosaccharides; the use of such methods to enable new structures to be generated from pre-existing oligosaccharides and for structural determinations of oligosaccharides; and the incorporation of such methods into automated systems.

BACKGROUND OF THE INVENTION

Saccharides (also known as sugars or carbohydrates), amino acids, fatty acids and nucleotides comprise the more major building blocks of biological macromolecules such as oligosaccharides, proteins, lipids and nucleic acids, respectively. Due to the diversity within a group of building blocks, such as saccharides for example, and the variety of ways in which to order the building blocks of a group or groups, large numbers of structurally distinct biological macromolecules are possible. Oligosaccharides alone, for example, are a group of biological polymers which comprise an extremely diverse group of molecules. Oligosaccharides exist as individual compounds as well as components of larger compounds. For example, a combination of an oligosaccharide and a protein is termed a glycoprotein. Similarly, a combination of an oligosaccharide and a lipid is termed a glycolipid. Oligosaccharides, glycoproteins and glycolipids have a large number of functions in nature. For example, these macromolecules in general, and their saccharide components in specific, serve as recognition molecules in a wide variety of normal and abnormal biological processes, including cancer and inflammation.

Because of the critical importance of oligosaccharides, alone or in combination with other molecules, there has been great interest in determining the structures of oligosaccharides and in making new oligosaccharides as well as portions of known oligosaccharides. An oligosaccharide is composed of individual saccharides, also known as monosaccharides. Typically, monosaccharides possess five carbon atoms (pentoses), six carbon atoms (hexoses), or are variants thereof. Regardless of whether there are five or six carbon atoms, each monosaccharide is capable of existing in five-atom ring forms (also known as five-membered rings or furanoses) and six-atom ring forms (also known as six-membered rings or pyranoses). For example, shown below are the five-membered ring (structure on left side) and the six-membered ring (structure on right side) for glucose:

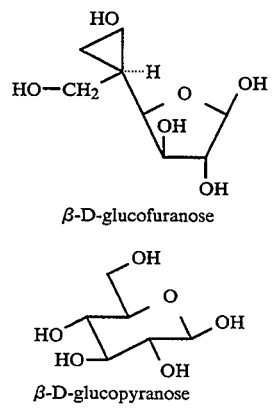

β-D-glucofuranose

β-D-glucopyranose

In addition, in solution, monosaccharides are in equilibrium between ringed forms (in which there is an oxygen in the ring) and open chain forms in which there is an aldehyde ("aldehydo") group in place of the bond between carbon-1 ("C-1") and the former ring oxygen. For example, shown below are ringed and open chain forms for glucose:

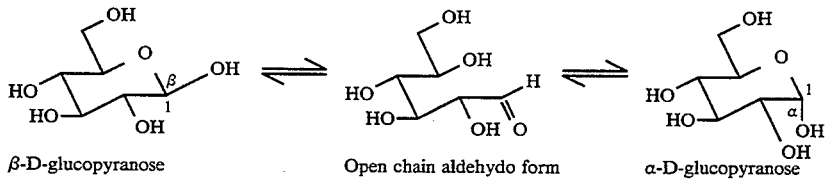

β-D-glucopyranose     Open chain aldehydo form     α-D-glucopyranose

Depending upon the arrangement of the substituents at C-1, the ring form may be the α anomer or β anomer as shown above. Since aldehydo groups may be reduced (i.e., converted to a lower oxidation state such as an alcohol), a monosaccharide which is capable of existing in an open chain aldehydo form is considered a reducing monosaccharide.

In all oligosaccharides, two or more individual saccharides (i.e., monosaccharides) are linked together to form an oligosaccharide. In oligosaccharides which bear a reducing monosaccharide, the other monosaccharides are always linked together with the linkage from C-1 of one monosaccharide to one of C-2, C-3, C-4, C-5 or C-6 of another monosaccharide. For example, shown below is an oligosaccharide in which glucose ("Glc") is linked to glucose from C-1 of the glucose on the left side to C-4 of the glucose on the right side:

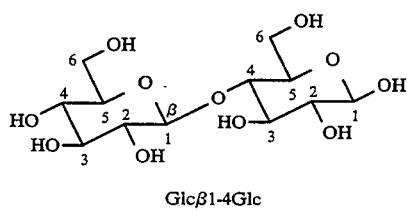

Glcβ1-4Glc

The linkage between the two glucose molecules may be α or β, depending upon the arrangement of the substituents at C-1. The glucose on the right side of the di-glucose oligosaccharide structure depicted above possesses an OH group (at C-1) which may exist as an aldehydo group and, therefore, is termed the "reducing end" of the oligosaccharide. Conversely, the glucose on the left side of the di-glucose structure depicted above does not possess an OH at C-1 and, therefore, is termed the "non-reducing end" of the oligosaccharide. In oligosaccharides that are linear (i.e., monosaccharides linked in a straight chain without branching), there will be one reducing end and one non-reducing end. However, if there is branching in an oligosaccharide (i.e., more than one monosaccharide is linked to a given monosaccharide), there will still be only one reducing end but two or more non-reducing ends. Since each monosaccharide may be linked to different positions of the given monosaccharide, there is the potential for oligosaccharides of significant complexity.

The current method for structural determination of oligosaccharides is based upon removal of monosaccharides from the non-reducing end(s). This approach is hampered by the fact that an analysis based upon removal from the non-reducing end(s) is a subtractive approach (i.e., compares the total monosaccharides, and the nature of their linkages, before and after removal to determine what is missing) and by the fact that where an oligosaccharide possesses more than one non-reducing end, additional information is necessary before the locations of the multiple non-reducing end monosaccharides may be affixed. Similarly, because a method for sequential removal of monosaccharides from the reducing end of an oligosaccharide has not been available, the preparation of new oligosaccharides or the isolation of portions of pre-existing oligosaccharides after removal of one or more monosaccharides from the reducing end of pre-existing oligosaccharides has not been possible. Thus, there is a need in the art for methods which permit the sequential removal of monosaccharides from the reducing end of oligosaccharides. The present invention fulfills these needs and further provides other related advantages.

SUMMARY OF THE INVENTION

Briefly stated, the present invention provides a variety of methods, which may be incorporated into systems which automate the reactions, related to the sequential removal of monosaccharides from the reducing end of oligosaccharides and structural determinations derived therefrom. In one aspect of the present invention, methods are provided for the sequential removal of monosaccharides from the reducing end of an oligosaccharide. In one embodiment, the method comprises the steps of: (a) generating from the monosaccharide at the reducing end of an oligosaccharide an aldehydo group or keto group on a carbon bonded to the carbon having the glycosidic linkage to an adjacent monosaccharide of the oligosaccharide, without introducing an aldehydo group or keto group on a ring carbon of any other monosaccharide of the oligosaccharide; and (b) cleaving the glycosidic bond between the former reducing end monosaccharide and the adjacent monosaccharide of the oligosaccharide using a hydrazine, thereby completing the removal of the former reducing end monosaccharide.

In another embodiment, the method comprises the steps of: (a) generating from the monosaccharide at the reducing end of an oligosaccharide an aldehydo group or keto group on a carbon bonded to the carbon having the glycosidic linkage to an adjacent monosaccharide of the oligosaccharide, without introducing an aldehydo group or keto group on a ring carbon of any other monosaccharide of the oligosaccharide; (b) cleaving the glycosidic bond between the former reducing end monosaccharide and the adjacent monosaccharide of the oligosaccharide using a hydrazine, thereby completing the removal of the former reducing end monosaccharide; and (c) converting the former adjacent monosaccharide to a free reducing monosaccharide.

In another embodiment, the method comprises the steps of: (a) reducing to an alcohol the aldehydo group or keto group of the open-chain form of the monosaccharide at the reducing end of an oligosaccharide without reducing any other functional groups of the oligosaccharide; (b) oxidizing vicinal diols of the monosaccharide at the former reducing end of the oligosaccharide without oxidizing vicinal diols or individual hydroxyl groups attached directly to ring carbons of the oligosaccharide, thereby generating from the monosaccharide an aldehydo group or keto group on a carbon bonded to the carbon having the glycosidic linkage to an adjacent monosaccharide of the oligosaccharide; and (c) cleaving the glycosidic bond between the former reducing end monosaccharide and the adjacent monosaccharide of the oligosaccharide using a hydrazine, thereby completing the removal of the former reducing end monosaccharide.

In yet another embodiment, the method comprises the steps of: (a) reducing to an alcohol the aldehydo group or keto group of the open-chain form of the monosaccharide at the reducing end of an oligosaccharide without reducing any other functional groups of the oligosaccharide; (b) oxidizing vicinal diols of the monosaccharide at the former reducing end of the oligosaccharide without oxidizing vicinal diols or individual hydroxyl groups attached directly to ring carbons of the oligosaccharide, thereby generating from the monosaccharide an aldehydo group or keto group on a carbon bonded to the carbon having the glycosidic linkage to an adjacent monosaccharide of the oligosaccharide; (c) cleaving the glycosidic bond between the former reducing end monosaccharide and the adjacent monosaccharide of the oligosaccharide using a hydrazine, thereby completing the removal of the former reducing end monosaccharide; and (d) converting the former adjacent monosaccharide to a free reducing monosaccharide.

In a related aspect of the present invention, methods are provided for the structural determination of an oligosaccharide. In one embodiment, the method comprises the steps of: (a) identifying the monosaccharide at the reducing end of an oligosaccharide; (b) determining the linkage between the reducing end monosaccharide and an adjacent monosaccharide; (c) generating from the monosaccharide at the reducing end of an oligosaccharide an aldehydo group or keto group on a carbon bonded to the carbon having the glycosidic linkage to an adjacent monosaccharide of the oligosaccharide, without introducing an aldehydo group or keto group on a ring carbon of any other monosaccharide of the oligosaccharide; (d) cleaving the glycosidic bond between the former reducing end monosaccharide and the adjacent monosaccharide of the oligosaccharide using a hydrazine, thereby completing the removal of the former reducing end monosaccharide; and (e) repeating steps (a) to (d).

In another embodiment, the method comprises the steps of: (a) identifying the monosaccharide at the reducing end of an oligosaccharide; (b) determining the linkage between the reducing end monosaccharide and an adjacent monosaccharide; (c) generating from the monosaccharide at the reducing end of an oligosaccharide an aldehydo group or keto group on a carbon bonded to the carbon having the glycosidic linkage to an adjacent monosaccharide of the oligosaccharide, without introducing an aldehydo group or keto group on a ring carbon of any other monosaccharide of the oligosaccharide; (d) cleaving the glycosidic bond between the former reducing end monosaccharide and the adjacent monosaccharide of the oligosaccharide using a hydrazine, thereby completing the removal of the former reducing end monosaccharide; (e) converting the former adjacent monosaccharide to a free reducing monosaccharide; and (f) repeating steps (a) to (e).

In another embodiment, the method comprises the steps of: (a) identifying the monosaccharide at the reducing end of an oligosaccharide; (b) determining the linkage between the reducing end monosaccharide and an adjacent monosaccharide; (c) reducing to an alcohol the aldehydo group or keto group of the open-chain form of the monosaccharide at the reducing end of the oligosaccharide without reducing any other functional groups on the oligosaccharide; (d) oxidizing vicinal diols of the monosaccharide at the former reducing end of the oligosaccharide without oxidizing vicinal diols or individual hydroxyl groups attached directly to ring carbons of the oligosaccharide, thereby generating from the monosaccharide an aldehydo group or keto group on a carbon bonded to the carbon having the glycosidic linkage to an adjacent monosaccharide of the oligosaccharide; (e) cleaving the glycosidic bond between the former reducing end monosaccharide and the adjacent monosaccharide of the oligosaccharide using a hydrazine, thereby completing the removal of the former reducing end monosaccharide; and (f) repeating steps (a) to (e).

In yet another embodiment, the method comprises the steps of: (a) identifying the monosaccharide at the reducing end of an oligosaccharide; (b) determining the linkage between the reducing end monosaccharide and an adjacent monosaccharide; (c) reducing to an alcohol the aldehydo group or keto group of the open-chain form of the monosaccharide at the reducing end of the oligosaccharide without reducing any other functional groups on the oligosaccharide; (d) oxidizing vicinal diols of the monosaccharide at the former reducing end of the oligosaccharide without oxidizing vicinal diols or individual hydroxyl groups attached directly to ring carbons of the oligosaccharide, thereby generating from the monosaccharide an aldehydo group or keto group on a carbon bonded to the carbon having the glycosidic linkage to an adjacent monosaccharide of the oligosaccharide; (e) cleaving the glycosidic bond between the former reducing end monosaccharide and the adjacent monosaccharide of the oligosaccharide using a hydrazine, thereby completing the removal of the former reducing end monosaccharide; (f) converting the former adjacent monosaccharide to a free reducing monosaccharide; and (g) repeating steps (a) to (f).

In another related aspect of the present invention, methods are provided for the cleavage of a glycosidic bond. In one embodiment, the method comprises reacting a hydrazine with a compound having the following formula:

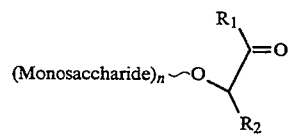

wherein the glycosidic bond between monosaccharide and O is $\alpha$ or $\beta$, n is 1 or more, and $R_1$ and $R_2$ are independently selected from H or an aliphatic group having from 1 to 8 carbon atoms with or without hydroxyl groups and with or without amino groups. In another embodiment, the method includes an additional second step of convening to a free reducing monosaccharide the monosaccharide formerly bonded directly to O.

These and other aspects of the present invention will become evident upon reference to the following detailed description and attached drawings.

DETAILED DESCRIPTION OF THE INVENTION

Figure 1:
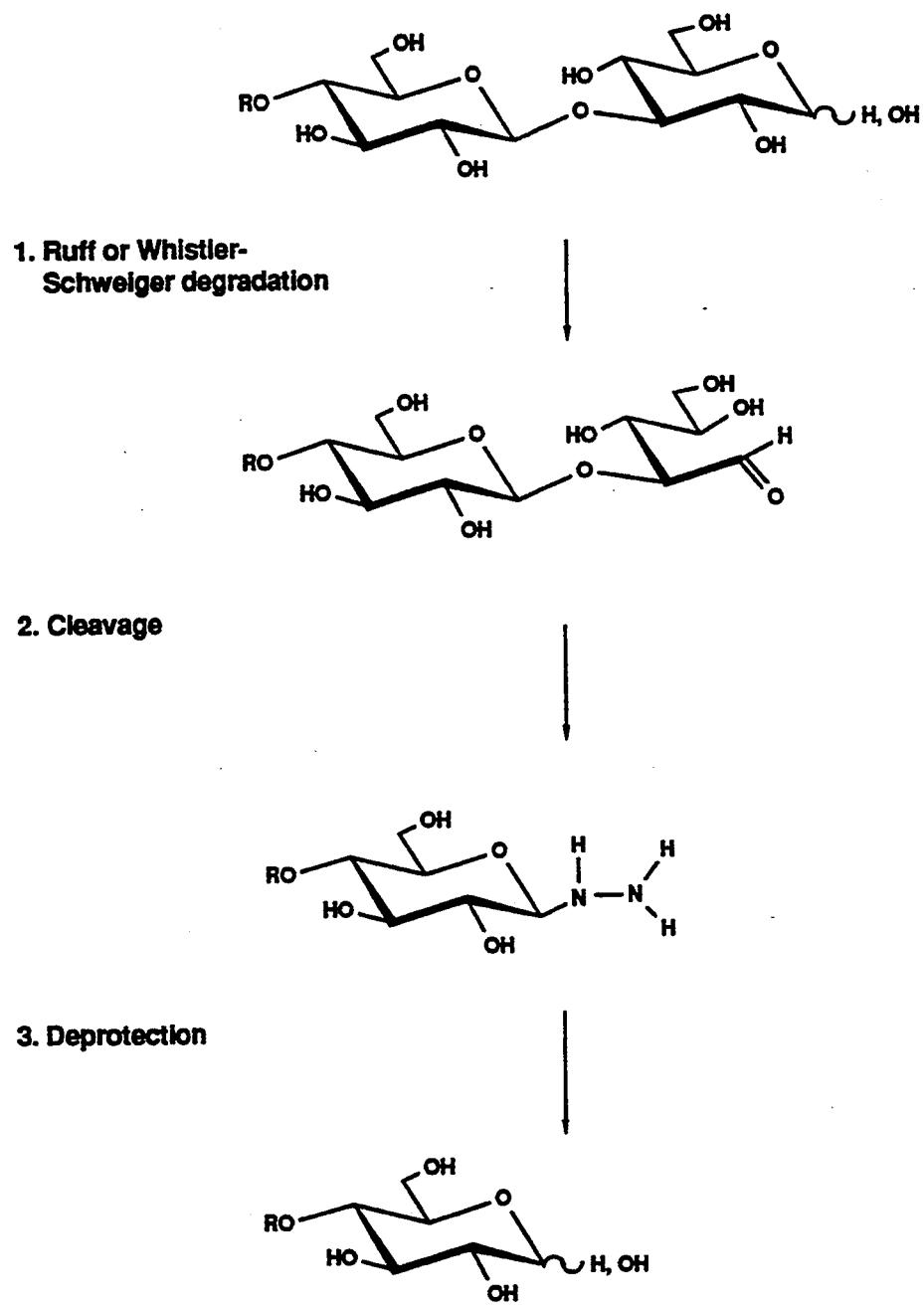
FIG. 1 illustrates the sequential removal of a monosaccharide from the reducing end of an oligosaccharide. In the first step, from the monosaccharide at the reducing end an aldehydo group is generated (e.g., by Ruff or Whistler-Schweiger degradation) on a carbon bonded to the carbon having the glycosidic linkage to the adjacent monosaccharide. In the second step, the former reducing end monosaccharide is cleaved with hydrazine. In the third step, the former adjacent monosaccharide is converted to a free reducing monosaccharide.
Figure 2:
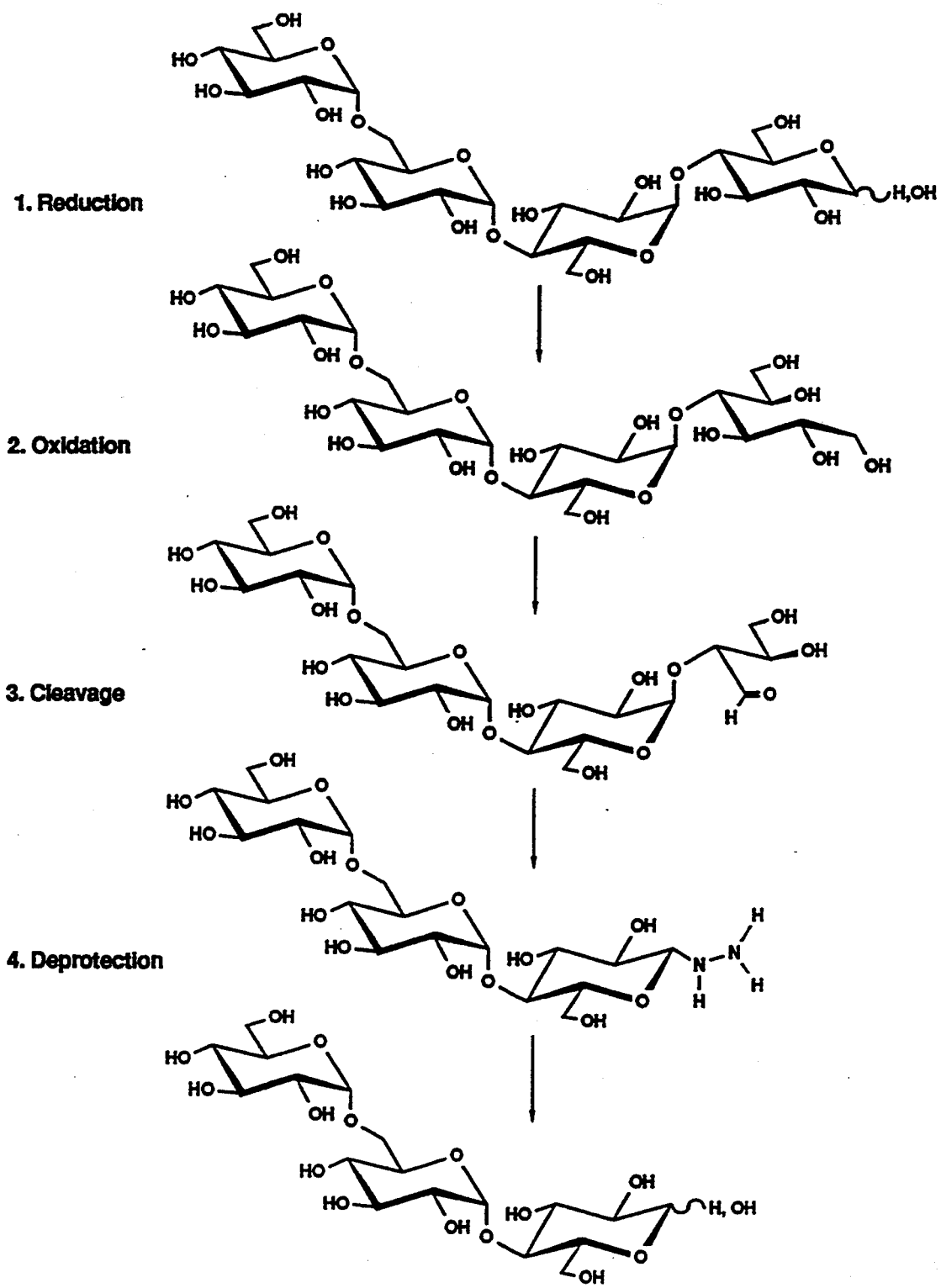
FIG. 2 illustrates the sequential removal of a monosaccharide from the reducing end of an oligosaccharide through the use of a reduction step and an oxidation step to generate an aldehydo group on a carbon bonded to the carbon having the glycosidic linkage to the adjacent monosaccharide. In the first step, the aldehydo group of the open-chain form of the monosaccharide at the reducing end (far right monosaccharide depicted) of the oligosaccharide is reduced. In the second step, by oxidation of a vicinal diol on the reducing end monosaccharide, an aldehydo group is formed on a carbon bonded to the carbon having the glycosidic linkage to the adjacent monosaccharide. In the third step, the former reducing end monosaccharide is cleaved with hydrazine. In the fourth step, the former adjacent oligosaccharide is converted to a free reducing monosaccharide.

As noted above, the present invention is directed toward methods related to the sequential removal of monosaccharides from the reducing end of an oligosaccharide, and the accomplishment of such methods in a manner which is susceptible to automation. As used herein, the term "oligosaccharide" refers to two or more monosaccharides (i.e., a disaccharide or greater) or derivatives thereof linked together in a linear or branched manner, and includes polysaccharides. The disclosure of the present invention shows that monosaccharides may be sequentially removed from the reducing end of an oligosaccharide. Because a reducing oligosaccharide will possess only one reducing end but may possess multiple non-reducing ends, an advantage of the methods and systems of the present invention is to permit removal of a single monosaccharide from a particular chain of monosaccharides, at a site which all reducing oligosaccharides have in common.

As disclosed within the present invention, monosaccharides may be removed one at a time from the reducing end of an oligosaccharide by essentially a two-step process. In the first step, an aldehydo group [i.e., HC(=O)—] or keto group [i.e., —C(=O)—] is generated, from the reducing end monosaccharide, on a carbon covalently bonded to the carbon which is glycosidically linked to an adjacent monosaccharide of the oligosaccharide. A glycosidic linkage between the reducing end monosaccharide and an adjacent monosaccharide refers to an oxygen which is interposed between, and joins, one monosaccharide to another by being bonded to a carbon atom on each of the two monosaccharides. In the process of generating such an aldehydo or keto group, one or more carbon atoms (and hydrogens or substituents attached thereto) may be lost from the reducing end monosaccharide.

The generation (from the reducing end monosaccharide) of an aldehydo or keto group on a carbon bonded to the carbon having the glycosidic linkage to an adjacent monosaccharide may be accomplished in a variety of ways, so long as an aldehydo or keto group is not introduced on a ring carbon of the other monosaccharide(s) of an oligosaccharide. Generation of an aldehydo or keto group on the desired carbon of the reducing end monosaccharide may be effected using one of numerous well-known reactions under conditions and for a time sufficient to permit generation. For example, an Amadori rearrangement (Micheel and Schleppinghoff, Chem. Ber. 89:1702–1708 (1956)) may be used to introduce a keto group adjacent to a glycosidic oxygen. In brief, as shown below, an amino compound is reacted with, for example, an aldose, and, depending upon the R groups, a 1-amino-2-keto compound results.

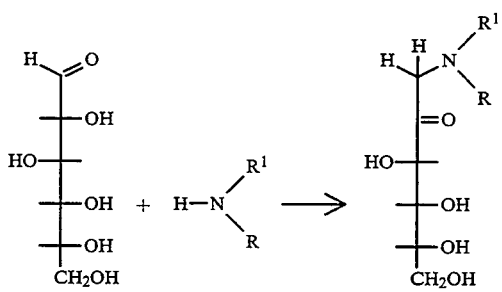

The specific reaction conditions vary depending primarily on the nature of the R and R' groups, but are typically performed in a temperature range from about 50° C.–100° C. in water, aqueous alcoholic solutions, dioxane, N,N-dimethylformamide, or tertiary amines, often with acetic, mercaptoacetic or 3-mercaptopropionic acids added.

Alternatively, reactions are available which cause a "Descent of the Series," i.e., hexose→pentose→tetrose, etc. Examples of this type of reaction are the Ruff degradation (Fletcher et al., J. Amer. Chem. Soc., 72:4546 (1950)) or the Whistler-Schweiger degradation (Whistler and Schweiger, J. Amer. Chem. Soc. 81:5190 (1959)) which is shown below.

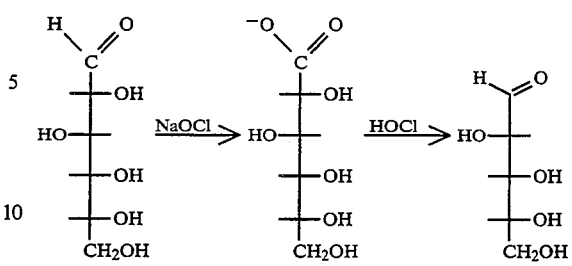

The procedure of Ruff is typically carried out in aqueous solution, in a temperature regime from about 0° C.–60° C. It involves two steps, first an oxidation of the monosaccharide aldehydo group to a carboxylic acid, typically effected by hypoiodite or bromine water. The second step employs a ferric salt and hydrogen peroxide to generate the aldose with one fewer carbon. The procedure of Whistler and Schweiger is a one-batch, two-stage procedure using hypochlorite, but varying the pH. As reported, it is conducted near room temperature (25° C.) in aqueous solution.

Another example of a "Descent of the Series" reaction is the Wohl degradation and variants thereof (Deulofeu, J. Chem. Soc. (1930), 2602; Weygand and Löwenfeld, Chem. Ber. 83:559 (1950)). This is a two-step procedure, first converting the reducing monosaccharide to an oxime derivative, typically carried out in aqueous solution or pyridine in a temperature range from about 0° C.–100° C. This step is followed by conversion, via a cyanohydrin, to the monosaccharide having one less carbon at the reducing end, using, for example, reagents such as 2,4-dinitrofluorobenzene in aqueous-alcohol mixtures from about 0° C.–100° C. or acetic anhydride followed by sodium methoxide in chloroform-methanol or silver oxide in aqueous-alcoholic ammonia mixtures, performed in the range of 0° C.–100° C.

An additional way to introduce a keto group on a carbon bonded to a carbon having a glycosidic linkage specifically at C-3 of a reducing monosaccharide is through formation of an arylosazone derivative. Removal of arylhydrazine groups generates a molecule having an aldehydo group at C-1 and a keto group at C-2 (an aldos-2-ulose, Mester and El Khadem, in The Carbohydrates Chemistry and Biochemistry, second edition, vol. IB, Pigman, W. and Horton D., eds., Academic Press, 1980).

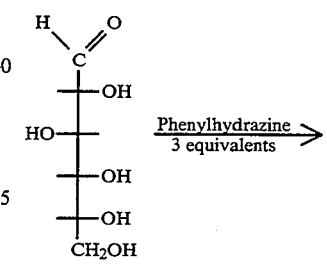

-continued

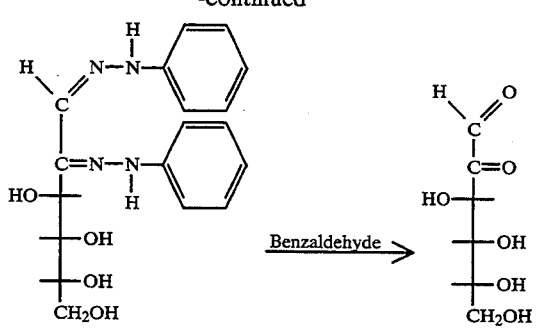

Arylosazones are typically formed by heating (40° C.–100° C.) aqueous solutions of arylhydrazines, often in the presence of sodium acetate, with reducing sugars.

It will be evident to those of ordinary skill in the art that combinations of the above reactions may be used to generate aldehydo groups or keto groups at desired carbons of the molecule. For example, a single "Descent of the Series" reaction would generate a pentose from a hexose; generation of a pentos-2-ulose after formation of an aryl osazone introduces a keto group at the former C-3 of the hexose molecule.

Yet another way to generate an aldehydo or keto group on the desired carbon of the reducing end monosaccharide is to combine a reduction step with a modified oxidation step. In the reduction step, the aldehydo or keto group which exists in the open-chain form of a reducing end monosaccharide may be selectively converted to an alcohol using a reducing agent under conditions and for a time sufficient to permit reduction. By selection of an appropriate reducing agent, no other functional groups on an oligosaccharide will be reduced. Examples of suitable reducing agents include borohydride reagents, such as sodium borohydride [these are available as a variety of salts, including cationic polymers in the borohydride form (for example, the polymer-supported borohydride reagents, products 32,864-2 and 35,994-7, Aldrich Chemical Co., Milwaukee, Wis.) and silica or alumina-supported sodium borohydride (products 24,361-2 and 24,362-0, Aldrich]; boron-centered hydrides also having covalent boron-carbon linkages, such as alkyl, or bulky groups, or cyano groups bonded directly to boron [members of this class include potassium tri-sec-butylborohydride (K-selectride, Aldrich, product 22,076-0), KS-selectride, lithium 9-BBN hydride, L-selectride, L-S-selectride, R-Alpine-hydride, and S-Alpine-hydride (products 22,077-9, 34,423-0, 25,704-4, 22,592-4, 22,902-4, and 23,772-8, respectively, Aldrich Chemical Co., Milwaukee, Wis.]; borane/diborane, often used as a complex with reagents such as triethylamine, diethylamine, t-butylamine, morpholine, pyridine, or tetrahydrofuran; aluminum hydride reagents, such as lithium aluminum hydride [these are available as other salts, such as sodium]; other aluminum-centered hydrides having covalently-linked carbons or alkoxy groups replacing hydrogens, such as diisobutylaluminum hydride [Aldrich, supplied as solutions in various solvents or sodium bis(2-methoxyethoxy)aluminum hydride (Red-Al , product 19,619-3, Aldrich Chemical Co., Milwaukee, Wis.]; catalytic hydrogenations, using hydrogen gas and various metals and prepared metal alloys, such as Raney nickel (a nickel-aluminum alloy) [a number of metals or alloys may be used to reduce aldehydo or keto groups, such as platinum, palladium, rhodium, ruthenium, or copper chromite, often supported on various inert materials, such as carbon, to increase surface area]; and dissolving metal reductions, using alkali metals (lithium, sodium, or potassium), as well as, for example, zinc, magnesium, tin, iron, or mercury in solvents such as alcohols, acetic acid, liquid ammonia, or ethers such as 1,2-dimethoxyethane.

An example of the reduction of glucose as the reducing end monosaccharide is shown below.

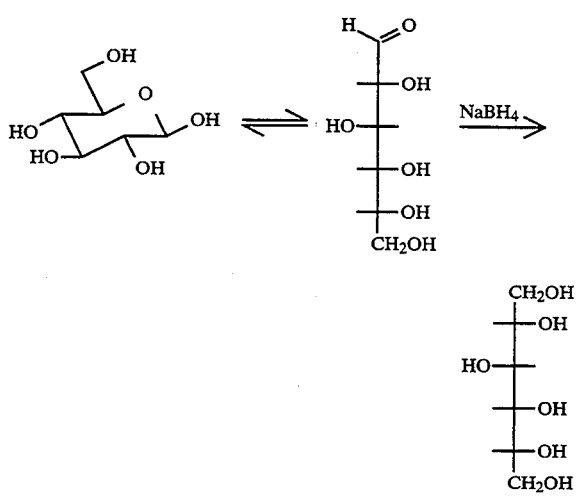

The reduction step may be performed under a variety of reaction conditions. Incubation of an oligosaccharide with a reducing agent is generally conducted within a temperature range from about 0° C. to 100° C., with a temperature of less than about 50° C.–60° C. being more typical. An incubation period of about 20 hours at room temperature is preferred. It will be appreciated by those of ordinary skill in the art that the time for exposure of an oligosaccharide to a reducing agent may be shortened or lengthened as the temperature is increased or decreased, respectively, from room temperature. A product of the reduction step may be examined by analytical techniques, such as $^1$H-NMR and mass spectroscopy. Yields may be checked very accurately (to within about 0.1%) through the use of the Park-Johnson ferricyanide procedure for aldehyde quantitation (Park and Johnson, J. Biol. Chem, 181:149–151 (1949)). In brief, by quantifying the color yield of a sample of the starting compound and then examining a sample of one hundred times as much of the product, if 1% of the starting material is present in the product, the same color yield will be observed in the two samples.

Reduction of the reducing end monosaccharide results in an additional hydroxyl group (i.e., —OH) on an open-chain form and prevents recyclization so that the reducing end monosaccharide is locked in an open-chain form. The carbon atom possessing the additional hydroxyl group is bonded to a carbon atom also possessing a hydroxyl group. Two hydroxyl groups attached to adjacent carbon atoms, respectively, are called "vicinal diols." Monosaccharides in their native form typically contain several vicinal diols. The monosaccharide which has been reduced is now referred to as the "former reducing end monosaccharide" because, although the monosaccharide is still attached to the oligosaccharide at its original position, its structure has been altered as described above by the reduction step.

Following the reduction step, the reduced oligosaccharide is treated under conditions and for a time sufficient such that the vicinal diols of the former reducing end monosaccharide are oxidized, but any vicinal diols or individual hydroxyl groups attached directly to ring carbons of other monosaccharide(s) of the oligosaccharide are not oxidized. Less common monosaccharides, such as sialic acid, possess vicinal diols which are indirectly attached (i.e., have one or more carbon atoms interposed) to the carbon atoms forming the monosaccharide ring. Such vicinal diols which are indirectly attached may be oxidized. However, by selection of an appropriate oxidizing agent under suitable conditions described below, there will be no significant oxidation of any vicinal diols or individual hydroxyl groups bonded directly to ring carbon atoms on monosaccharides (other than the former reducing end monosaccharide) of an oligosaccharide.

The oxidation step will result in the loss of one or more carbon atoms (and hydrogens and substituents attached thereto) from the former reducing end monosaccharide. In any case, the product of the oxidation step will be an oligosaccharide whose former reducing end monosaccharide now possesses an aldehydo or keto group on a carbon bonded to the carbon having the glycosidic linkage to an adjacent monosaccharide. Examples of suitable oxidizing agents include lead tetraacetate, periodic acid or its salts (such as sodium or lithium), sodium bismuthate (Rigby, *J. Chem, Soc.* 1907–1913 (1950)); manganese (III) pyrophosphate (Levesley et al., *J. Chem. Soc.* 840–845 (1956)); phenyliodosoacetates (Criegee and Beucker, *Ann. Chem.* 541:218–238 (1939)); vanadium (V) salts (Littler et al., *J. Chem. Soc.* 2761–2766 (1960)); nickel peroxide (Konika and Kuruma, *J. Org. Chem.* 36:1703–1704 (1971)); silver(I) and peroxy disulfate (Huyser and Rose, *J. Org. Chem.* 37:851–853 (1972)); cerium (IV) salts (Duke and Forist, *J. Amer. Chem. Soc.* 71:2790 (1949)); xenic acid (Jaselskis and Vas, *J. Amer. Chem. Soc.* 86:2078–2079 (1964)); and thallium (III) salts (McKillop et al., *J. Org. Chem.* 37:4204–4206 (1972)).

An example of the oxidation of 2-acetamido-2-deoxy-4-O-(2-acetamido-2-deoxy-β-D-glucopyranosyl)-D-glucitol is shown below.

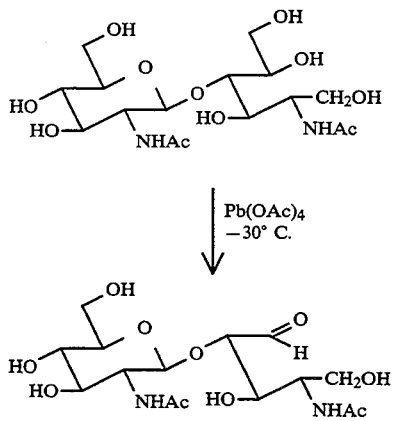

The oxidation step may be performed under a variety of reaction conditions. Incubation of a reduced oligosaccharide with an oxidizing agent is generally conducted within a temperature range from about −80° C. to about 50° C., with a temperature of about 0° C. or colder being typical and a temperature of about −20° C. or colder being preferred. An incubation period of about 1 hour at a temperature of about −20° C. or colder is preferred. It will be appreciated by those of ordinary skill in the art that the time for exposure of a reduced oligosaccharide to an oxidation agent may be shortened or lengthened as the temperature is increased or decreased, respectively, from the range of about 50° C. to −80° C. A product of the oxidation step may be examined by analytical techniques, such as $^1$H-NMR and mass spectroscopy.

Given the teachings provided herein, it would be evident to those of ordinary skill in the art that other methods may be utilized for generation of an aldehydo or keto group on a carbon bonded to the carbon having the glycosidic linkage to a monosaccharide adjacent to the reducing end monosaccharide. Further, it would also be evident that if two or more monosaccharides are glycosidically-linked to a single reducing monosaccharide that aldehydo or keto groups may be generated on those carbons bonded to the carbons involved in the glycosidic linkages to the respective monosaccharides.

After an aldehydo or keto group has been generated (whether by reduction+oxidation, or otherwise) on the carbon of a reducing end monosaccharide which is bonded to a carbon having the glycosidic linkage to an adjacent monosaccharide, the glycosidic linkage is cleaved using a hydrazine under conditions and for a time sufficient to permit cleavage. Where there are two or more aldehydo or keto groups as a result of the presence of more than one monosaccharide being attached to the reducing end monosaccharide, those glycosidic linkages which have an aldehydo or keto group bonded to a carbon participating in the glycosidic linkage are cleaved by a hydrazine. As used herein, the term "hydrazine" refers to hydrazine as well as alkyl, acyl, and heteroatom hydrazine derivatives. Examples of suitable hydrazines include hydrazine; alkylhydrazines, such as methylhydrazine; arylhydrazines, such as 3-(trifluoromethyl)phenylhydrazine; semicarbazides, such as semicarbazide; thiosemicarbazides, such as thiosemicarbazide; carbohydrazides, such as carbohydrazide; thiocarbohydrazides, such as thiocarbohydrazide; acylhydrazides, such as benzoylhydrazide; sulfonylhydrazides, such as p-tolylsulfonylhydrazine; phosphorohydrazides, such as diphenylphosphorohydrazide; dithiocarbazates, such as dithiocarbazic acid; and thiophosphorohydrazides, such as dimethoxy(thiophosphoro)-hydrazide.

A primary amino group of a hydrazine will first bond to the carbon of the former reducing end monosaccharide which bears the newly generated aldehydo or keto group, and then the glycosidic linkage will be cleaved by an intramolecular reaction. When the hydrazine is present in excess, not only will the reaction result in cleavage of the glycosidic bond, but also another molecule of the hydrazine will react with the new reducing end monosaccharide, thereby converting this monosaccharide to the hydrazone-cyclic hydrazine derivative. The reaction mechanism for cleavage with a hydrazine is shown below.

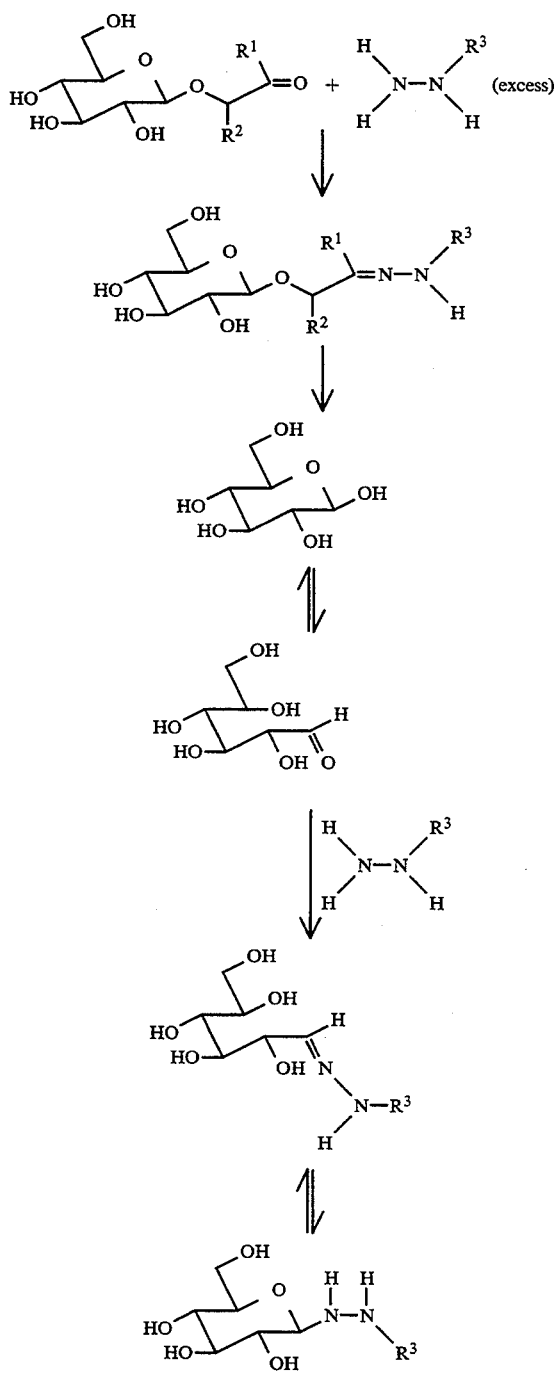

Similar to the previous reaction steps, the glycosidically-linked monosaccharide may be any monosaccharide, in α or β linkage. The cleavage step may be performed under a variety of reaction conditions. Incubation of a hydrazine with an oligosaccharide possessing a former reducing end monosaccharide is generally conducted under an inert atmosphere (e.g., argon or nitrogen) within a temperature range from about 0° C. to 150° C., with a temperature of about 50° C.-70° C. being typical. An incubation period of about 20-24 hours at 55° C.-70° C. is preferred. It will be appreciated by those of ordinary skill in the art that the time and temperature may be varied. A product of the cleavage step may be examined by analytical techniques, such as $^1$H-NMR and mass spectroscopy.

The cleavage step may be used for the cleavage of a glycosidic bond, either independently or as part of an overall method for the sequential removal of monosaccharides from the reducing end of an oligosaccharide. In either scenario, a variety of structures may be glycosidically linked to one or more monosaccharides. An example of a structure amenable to cleavage at the glycosidic linkage by a hydrazine is shown below.

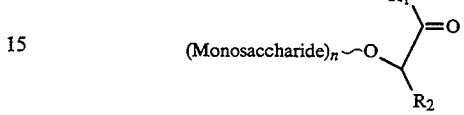

Either $R_1$ or $R_2$ may be hydrogen or an aliphatic group, or both $R_1$ and $R_2$ may be hydrogen or an aliphatic group. An aliphatic group is preferably from about 1 to 8 carbon atoms and may have attached thereto either one or more hydroxyl groups, or one or more amino groups, or both. As used herein, the term "amino groups" includes derivatives, such as modifications of amino groups to N-acyl groups (such as N-acetyl groups), N-alkyl groups, or N-aryl groups. Where an unmodified monosaccharide is desired, it would be preferable to conduct the cleavage reaction under conditions (such as those described above) which either release the monosaccharide without modification, or convert it to a derivative which permits the monosaccharide to be recovered without modification.

It will be evident to those of ordinary skill in the art that the aldehydo group or keto group, bonded to a carbon having the glycosidic linkage to an adjacent monosaccharide, may be temporarily blocked by another functional group (hereinafter referred to as a "blocking group") en route to reaction with a hydrazine. Blocking groups are defined as reagents which reversibly react with an aldehydo or keto group and which can be removed with other specific reagents prior to the cleavage step with a hydrazine, or may be removed with a hydrazine itself prior to or concurrent with the cleavage step. Such blocking groups include acetals, ketals, dithioacetals, hemithioacetals, imines, and O-substituted cyanohydrins.

Where an excess of a hydrazine has been used during the cleavage step, it may be desirable to deprotect the new reducing end monosaccharide, i.e., treating under conditions and for a time sufficient such that the hydrazone-cyclic hydrazine derivative is converted to a free reducing monosaccharide. Examples of suitable deprotecting agents include N-acylating reagents followed by mild acid treatment, benzaldehyde (Fischer and Armstrong, Chem. Ber. 35:3141–3144 (1902)); nitrous acid (Ohle et al., Chem. Ber. 86:316–321 (1953)); and copper(II) salts (El Khadem, J. Chem. Soc. 3452–3453 (1953)). Acyl groups may be introduced using anhydrides or acylchorides, using, for example, reagents such as acetic anhydride, acetyl chloride, propionic anhydride, or trimethylacetic anhydride. Ketene has also been used for selective N-acetylation.

An example of the deprotection of glucose is shown below.

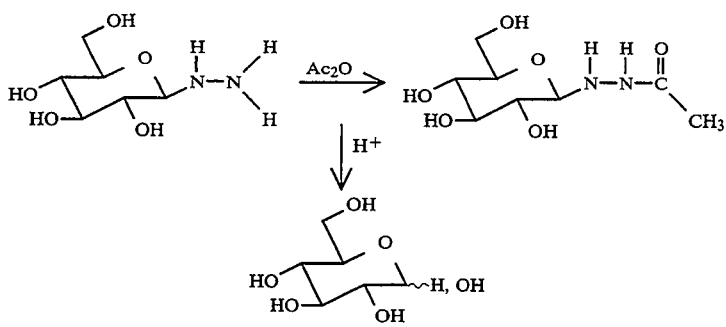

Deprotection may be accomplished by a variety of techniques which do not cleave glycosidic linkages. Incubation of an oligosaccharide possessing a blocked reducing end monosaccharide with a deprotecting agent is generally conducted within a temperature range from about 0° C. to 100° C., with a temperature of about 20° C. to 40° C. being more typical. An incubation period of about 1 hour at room temperature is preferred. Where a monosaccharide is blocked using hydrazine itself, removal by N-acylation followed by mild acid treatment is preferred. Where a monosaccharide is blocked using a substituted hydrazine derivative, removal with benzaldehyde or Cu(II) salts is preferred. It will be appreciated by those of ordinary skill in the art that the time and temperature may be varied. A product of the deprotection step may be examined by analytical techniques, such as $^1$H-NMR and mass spectroscopy.

It will be evident to those of ordinary skill in the art that any or all of the various reaction steps described above may be performed under liquid phase or solid phase conditions. Typically in solid phase methodology, a reactant or reagent is immobilized on a solid support such as glass beads, polymeric matrices, scintered glass discs, fiberglass membranes, or polymeric membranes. For example, a hydrazine may be covalently linked (e.g., directly or via a crosslinking agent) to a chromatography resin and an oligosaccharide, with a new aldehydo or keto group on the former reducing monosaccharide, brought in contact with the resin under conditions and for a time sufficient to permit cleavage, or cleavage and blocking. Alternatively, an oligosaccharide may be immobilized (e.g., via a non-reducing end monosaccharide) and contacted with the various reactants in a step-wise manner with one or more wash steps interposed where desired.

It will be apparent that the various reaction steps described above, whether performed under liquid phase or solid phase conditions, may be incorporated into a system which automates the reactions. Such a system is typically in an instrument format. A system may be comprised of multiple reaction vessels, where within each vessel a single chemical reaction is performed. In such a system, an oligosaccharide is transported from vessel to vessel to accomplish the overall series of reactions. For example, an oligosaccharide may be introduced into a first vessel where the appropriate reagents are contained (or introduced) such that generation of an aldehydo group or keto group on the desired carbon of the reducing end monosaccharide is effected. The oligosaccharide possessing a modified reducing end monosaccharide is then transported to a second vessel where a cleavage step (as described above) occurs. Additional vessels may be incorporated into a system where additional reactions, such as the deprotection reaction described above, are desired. Alternatively, a system may be comprised of a single reaction vessel, where all the chemical reactions are performed step-wise by the sequential addition and removal of the appropriate reagents. In such a system, an oligosaccharide may be immobilized within the reaction vessel and the necessary reagents for a particular reaction introduced under conditions and for a time sufficient to effect the reaction. Following completion of a reaction step, the reaction vessel is flushed to remove any reagents and by-products, leaving the immobilized, modified oligosaccharide. A new set of reagents is introduced, reacted, and the removal process repeated to accomplish a second reaction step in a series of reactions. It will be evident to those of ordinary skill in the art that a variety of ways exist for automating the methods of the present invention.

The sequential removal of monosaccharides from the reducing end of an oligosaccharide has a number of uses. For example, the disclosure of the present invention permits the preparation of new oligosaccharides. By the removal of one or more monosaccharides from the reducing end of an oligosaccharide, or from both the reducing and non-reducing ends, new structures which are derived from existing oligosaccharides may be prepared. Alternatively, after such removal of one or more monosaccharide, other monosaccharides or non-carbohydrate molecules may be chemically or enzymatically joined to the partially degraded oligosaccharide to form new molecules.

Another use of the sequential removal of monosaccharides from the reducing end is to facilitate the structural determination of an oligosaccharide. The methods of the present invention for sequential removal of monosaccharides from the reducing end of an oligosaccharide may be combined with methods, for identifying the reducing end monosaccharide and for determining its linkage to an adjacent monosaccharide, in order to provide methods for the structural determination of an oligosaccharide. It will be evident to those of ordinary skill in the art that a variety of methods exist for identifying the reducing end monosaccharide and for determining the linkage between the reducing end monosaccharide and an adjacent monosaccharide.

For example, a monosaccharide at the reducing end of an oligosaccharide may be identified through reactions specific to the aldehydo or keto group; other monosaccharides in the molecule are unable to undergo such reactions, lacking the ability to enter into the open-chain form. The modified monosaccharide at the former reducing end must be stable to acid hydrolysis under conditions which cleave the glycosidic linkages in the molecule, thereby permitting identification of the former reducing monosaccharide based on a comparison of the properties of the derivatized molecule (chromatographic or otherwise, such as NMR or mass spectroscopy) to similarly-derivatized monosaccharide standards. Such reactions include: (1) reduction; (2) conversion to an imine, followed by reduction; (3) conversion to a hydrazone derivative, followed by reduction; or (4) oxidation of an aldehydo group to a carboxyl group. Reduction may be effected by a number of reagents, such as sodium borohydride. These reagents permit the aldehydo or keto group of the reducing monosaccharide to be reduced to an alcohol. Reagents (for example, sodium borotritiide) may also permit a radiolabelled hydrogen (tritium) to be introduced, permitting the alditols to be selectively identified as radiolabelled components. In conversion to an imine, followed by reduction, the aldehydo or keto group of the reducing monosaccharide reacts with amino compounds, such as 2-pyridylamine, to generate imino products. These may be reduced with a number of the above reducing reagents (such as sodium cyanoborohydride or borane complexed with, for example, diethylamine, triethylamine, or pyridine) giving covalent C-1 derivatives which survive acid hydrolysis. The former reducing monosaccharide can be identified based on chromatographic comigration with standards, or other properties of the molecules. In conversion to a hydrazone derivative, followed by reduction, the aldehydo or keto group of the reducing monosaccharide reacts with hydrazine compounds, such as hydrazine, to generate hydrazine products. These may be reduced with a number of the previously-described reagents to give covalent hydrazine products which survive acid hydrolysis. The former reducing monosaccharide can be identified based on chromatographic comigration with standards, or other properties of the molecules. In oxidation of an aldehydo group to a carboxyl group (using reagents such as bromine water or sodium hypoiodite), the product so generated is an aldonic acid, which can be identified after acid hydrolysis based on chromatographic or other properties of the molecules. The aldonic acids may also be further derivatized as esters, amides, or hydrazides at C-1, and compared to similarly-derivatized standards. It will be appreciated by those of ordinary skill in the art that the aldehydo groups or keto groups generated by oxidation of the former reducing monosaccharide, or their generation at the reducing monosaccharide by any of the aforementioned methods, either alone or in combination, may be derivatized by any of the same reagents specific to the aldehydo or keto group, above, and that these structures may be amenable in the same way to the above analyses in order to obtain information concerning the position of a glycosidically-linked substituent.

Characterization of the linkage(s) between the reducing end monosaccharide and an adjacent monosaccharide(s) may be accomplished, for example, by permethylation analysis. By permethylating an oligosaccharide, the hydroxyl groups will be converted to methyl ethers (—OH →—OCH$_3$), thereby yielding derivatized monosaccharides. The oligosaccharide is then hydrolyzed to yield the constituent monosaccharides. Typically, the derivatized monosaccharides are analyzed by GC-MS (gas chromatography-mass spectroscopy) and the linkage determined by a subtractive method. However, those of ordinary skill in the art will recognize that many of the aforementioned reagents for permitting identification of the former reducing end monosaccharide through reactions specific to the aldehydo or keto group may also be utilized prior to the permethylation procedure. Hence, the permethylated monosaccharide derivative located solely at the former reducing end of the oligosaccharide may be selectively determined after hydrolysis of glycosidic linkages by chromatographic or other comparisons to similarly-derivatized standards, thereby permitting its linkage to be selectively determined.

It will be appreciated by those of ordinary skill in the art that separate aliquots of an oligosaccharide sample will be used to perform the overall structural determination where the method for identifying the reducing monosaccharide, or the method for determining its linkage, modify monosaccharides other than the reducing end monosaccharide or cleave the glycosidic linkages between the individual monosaccharides of an oligosaccharide. For example, one aliquot may be used to identify the reducing end monosaccharide and to determine its glycosidic linkage, and another aliquot used to sequentially remove the reducing end monosaccharide. Alternatively, separate aliquots may be used for identification of the reducing monosaccharide and for determination of its glycosidic linkage. Where more than one aliquot of an oligosaccharide sample is used in the overall structural determination, those of ordinary skill in the art will recognize that the order in which the identification (of the reducing end monosaccharide), the determination (of the glycosidic linkage), and the sequential removal (of the reducing end monosaccharide) steps are performed does not alter the final result and, therefore, may be varied. By the combination of methods for the identification of the reducing end monosaccharide, determination of its glycosidic linkage, and the sequential removal of the reducing end monosaccharide, the structure of an oligosaccharide may be determined.

To summarize the examples which follow, Example 1 describes the reduction of the reducing end monosaccharides of oligosaccharides. Example 2 describes the oxidation of oligosaccharides whose monosaccharide at the reducing end has been reduced. Example 3 describes the cleavage of former reducing end monosaccharides from oligosaccharides. Example 4 describes removal of a hydrazine product from monosaccharides which were formerly adjacent to their respective reducing end monosaccharide.

The following examples are offered by way of illustration and not by way of limitation.

EXAMPLES

EXAMPLE 1

Reduction of Oligosaccharides

A. 2-acetamido-2-deoxy-4-O-(2-acetamido-2-deoxy-$\beta$-D-glucopyranosyl)-D-glucose ($\beta$-D-GlcpNAc-(1-4)-D-GlcNAc)

This oligosaccharide (41.2 $\mu$mol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H$^+$ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 2-acetamido-2-deoxy-4-O-(2-acetamido-2-deoxy-β-D-glucopyranosyl)-D-glucitol; 99.6% yield.

B. 4-O-(4-O-[6-O-α-D-glucopyranosyl-α-D-glucopyranosyl]-α-D-glucopyranosyl)-D-glucose (α-D-Glcp-(1-6)-α-D-Glcp-(1-4)-α-D-Glcp-(1-4)-D-Glc)

This oligosaccharide (42.1 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 4-O-(4-O-[6-O-α-D-glucopyranosyl-α-D-glucopyranosyl]-α-D-glucopyranosyl)-D-glucitol; 99.6% yield.

C. 6-O-(2-acetamido-2-deoxy-4-O-[β-D-galactopyranosyl]-β-D-glucopyranosyl)-D-galactopyranose (β-D-Galp-(1-4)-β-D-GlcpNAc-(1-6)-D-Gal)

This oligosaccharide (18.3 μmol) was dissolved in 1.0 mL distilled water. Sodium borohydride (1.0 mmol) was added and the solution left for 20 hours at room temperature (~22° C.). Distilled water (4.0 mL) was added, followed by 1.0 mL of 2.0M acetic acid. After 1 hour, the sample was loaded on a well-washed column (6.0 mL) of Dowex AG50W-X8, H+ form, 100–200 mesh, and the eluent collected. It was washed with four additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 6-O-(2-acetamido-2-deoxy-4-O-[β-D-galactopyranosyl]-β-D-glucopyranosyl)-D-galactitol; >99% yield.

D. 4-O-(β-D-glucopyranosyl)-D-glucose (β-D-Glcp-(1-4)-D-Glc)

This oligosaccharide (56.1 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 4-O-(β-D-glucopyranosyl)-D-glucitol; 100.0% yield.

E. 2-acetamido-2-deoxy-3-O-(β-D-galactopyranosyl)-D-galacctose (β-D-Galp-(1-3)-D-GalNAc)

This oligosaccharide (44.3 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 2-acetamido-2-deoxy-3-O-(β-D-galactopyranosyl)-D-galactitol; 99.9% yield.

F. 6-O-α-D-galactopyranosyl-D-glucose (α-D-Galp-(1-6)-D-Glc)

This oligosaccharide (73.2 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 6-O-α-D-galactopyranosyl-D-glucitol; 99.9% yield.

G. 6-O-α-D-glucopyranosyl-D-glucose (α-D-Glcp-(1-6)-D-Glc)

This oligosaccharide (51.6 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 6-O-α-D-glucopyranosyl-D-glucitol; 100.0% yield.

H. 3-O-α-D-mannopyranosyl-D-mannose (α-D-Manp-(1-3)-D-Man)

This oligosaccharide (28.3 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 3-O-α-D-mannopyranosyl-D-mannitol; >98% yield.

I. 3-O-α-D-glucopyranosyl-D-glucose (α-D-Glep-(1-3)-D-Glc)

This oligosaccharide (97.6 gmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 3-O-α-D-glucopyranosyl-D-glucitol; 98.3% yield.

J. 4-O-(6-O-α-D-glucopyranosyl-α-D-glucopyranosyl)-D-glucose (α-D-Glcp-(1-6)-α-D-Glcp-(1-4)-D-Glc)

This oligosaccharide (33.7 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 4-O-(6-O-α-D-glucopyranosyl-α-D-glucopyranosyl)-D-glucitol; 99.6% yield.

K. 6-O-(2-acetamido-2-deoxy-β-D-glucopyranosyl)-D-galactose (β-D-GlcNAcp-(1-6)-D-Gal)

This oligosaccharide (60.1 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 6-O-(2-acetamido-2-deoxy-β-D-glucopyranosyl)-D-galactitol; 99.0% yield.

L. 2-acetamido-2-deoxy-4-O-(β-D-galactopyranosyl)-D-glucose (β-D-Galp-(1-4)-D-GlcNAc)

This oligosaccharide (58.1 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 2-acetamido-2-deoxy-4-O-(β-D-galactopyranosyl)-D-glucitol; 99.7% yield.

M. 4-O-β-D-galactopyranosyl-D-glucose (β-D-Galp-(1-4)-D-Glc)

This oligosaccharide (51.6 μmol) was dissolved in 1.0 mL distilled water. Sodium borohydride (1.0 mmol) was added and the solution left for 18 hours at room temperature (~22° C.). Distilled water (4.0 mL) was added, followed by 1.0 mL of 2.0M acetic acid. After 1 hour, the sample was loaded on a well-washed column (5.0 mL) of Dowex AG50W-X8, H+ form, 100–200 mesh, and the eluent collected. It was washed with three additional 5.0 mL washes of water. The total eluent was rotary evaporated to dryness. Boric acid was removed by rotary evaporation to dryness five times with approximately 10 mL of a solution containing 1.0% (vol/vol) acetic acid in methanol, followed by rotary evaporation to dryness three times with about 10 mL of methanol alone. The product was 4-O-β-D-galactopyranosyl-D-glucitol; 99.9% yield.

EXAMPLE 2

Oxidation of Reduced Oligosaccharides

A. 2-acetamido-2-deoxy-4-O-(2-acetamido-2-deoxy-β-D-glucopyranosyl)-D-glucitol (β-D-GlcpNAc-(1-4)-D-GlcNACitol)

This reduced oligosaccharide (0.5 μmol in 50 μL water) was dissolved in 4.0 mL of a solution containing 1:1 (vol/vol) methylsulfoxide (anhydrous, Aldrich) and glacial acetic acid. The solution was placed in the bottom of a flask having a sidearm capable of holding 6.0 mL when tilted (Kontes Glass, article 881675-0125). The flask was lowered into a methanol bath at −30° C., maintained in a Haake-Buchler F3-Q Cryostat. A freshly-prepared solution containing 0.5 mmol of lead tetraacetate dissolved in 6.0 mL of 1:1 (vol/vol) methylsulfoxide:glacial acetic acid was introduced into the sidearm of the flask, and both solutions were cooled for 20 minutes at −30° C., stoppering the flask to prevent water condensation. The flask was tilted to start the reaction at −30° C., and kept for 1 hour at −30° C. The flask could be tilted, after about 40 minutes, to permit the stopping solution to be introduced into the sidearm and to allow it to cool. The stopping solution was comprised of 1.0 mL methylsulfoxide, 1.0 mL glacial acetic acid, and 0.5 mL 2,3-butanediol (Aldrich, product B8,490-4). After the 1 hour reaction, the flask was tilted to introduce the stopping solution into the reaction mixture. It was kept for another hour at −30° C., and then removed from the cooling bath. Distilled water (15 mL) was added. The solution was run through a well-washed column (5.0 mL) of Dowex AG50W-X8, H+ form, 100–200 mesh, followed by three 5.0 mL washes with water. The solution was rotary evaporated to remove volatile materials, and was placed under high vacuum (<100 mTorr) overnight. The product was 4-acetamido-4-deoxy-2-O-(2-acetamido-2-deoxy-β-D-glucopyranosyl)-L-xylose; 96% yield.

B. 4-O-(6-O-α-D-glucopyranosyl-α-D-glucopyranosyl)-D-glucitol (α-D-Glcp-(1-6)-α-D-Glcp-(1-4)-D-Glcitol)

This reduced oligosaccharide (3.2 μmol) was dissolved in 4.0 mL of a solution containing 1:1 (vol/vol) N,N-dimethylformamide (Aldrich, anhydrous) and distilled water. The solution was placed in the bottom of a flask having a sidearm capable of holding 4.0 mL when tilted (Kontes Glass, article 881675-0125). The flask was lowered into a methanol bath at −20° C., maintained by a Haake-Buchler F3-Q cryostat. A freshly prepared solution containing 0.25 mmol periodic acid in 4.0 mL of 1:1 N,N-dimethylformamide:water was introduced into the sidearm of the flask, and both solutions were cooled for 20 minutes at −20° C., stoppering the flask to prevent water condensation. The flask was tilted to start the reaction at −20° C., and kept for 1 hour at −20° C. The flask could be tilted, after 40 minutes, to permit the stopping solution to be introduced into the sidearm and to allow it to cool. The stopping solution was comprised of 0.75 mL water, 0.75 mL N,N-dimethylformamide, and 0.5 mL 2,3-butanediol (Aldrich, product B8,490-4). After the 1 hour reaction, the flask was tilted to introduce the stopping solution into the reaction mixture. It was kept for another hour at −20° C., and then removed from the cooling bath. Distilled water (15.0 mL) was added. The sample was run through a well-washed column (5.0 mL) of Dowex AG1-X8, acetate form, 100–200 mesh, followed by three 5.0 mL washes with water. The sample was rotary evaporated to remove volatile materials and was placed under high vacuum (<100 mTorr) overnight. The product was 2-O-(6-O-α-D-glucopyranosyl-α-D-glucopyranosyl)-D-erythrose; 88% yield.

C. 6-O-(2-acetamido-2-deoxy-4-O-[β-D-galactopyranosyl]-β-D-glucopyranosyl)-galactitol (β-D-Galp-(1-4)-β-D-GlcpNAc-(1-6)-Galitol)

This reduced oligosaccharide (10 μmol) was dissolved in a solution containing 1.0 mL distilled water, 3.0 mL glacial acetic acid, and 9.0 mL methanol. The mixture was placed in the bottom of a flask having a sidearm capable of holding 6.5 mL when tilted (Kontes Glass, article 881675-0125), along with a magnetic stir bar. The flask was lowered into an ethanol bath maintained at −76° C. with solid carbon dioxide, and allowed to cool for 15 minutes. The flask should be stoppered to prevent condensation. Lead tetraacetate (0.5 mmol) was added, and the solution stirred for 1 hour. The flask could be tilted, after 40 minutes, to permit the stopping solution to be introduced into the sidearm and to allow it to cool. The stopping solution was comprised of a mixture of 0.48 mL distilled water, 1.43 mL glacial acetic acid, 4.31 mL methanol, and 0.28 mL ethylene glycol. After the 1 hour reaction, the flask was tilted to introduce the stopping solution into the reaction mixture. It was kept for another hour at −76° C., and then removed from the cooling bath. Distilled water (20.0 mL) was added. The mixture was rotary evaporated down to about 5.0 mL. It was then loaded on a column (5.0 mL) of Dowex AG50W-X8, H+ form, followed by three 5.0 mL washes of water. The total eluent was rotary evaporated to reduce the volume to about 3.5 mL and loaded on a column (1.5×95 cm) of well-washed Sephadex G-10 (40–120 μm bead size), run in water. Fractions containing the oligosaccharide product were pooled. The product was 2-O-(2-acetamido-2-deoxy-4-O-[β-D-galactopyranosyl]-β-D-glucopyranosyl)-glycolaldehyde; >95% yield.

D. 6-O-(2-acetamido-2-deoxy-β-D-glucopyranosyl)-galactitol (β-D-GlcpNAc-(1-6)-Galitol)

This reduced oligosaccharide (5.0 μmol) was dissolved in 5.0 mL distilled water. The solution was placed in the bottom of a flask having a sidearm capable of holding 5.0 mL when tilted (Kontes Glass, article 881675-0125). The flask was lowered into an ice-water bath at 0° C. A solution containing 1.0 mmol of periodic acid in 5.0 mL water was introduced into the sidearm of the flask, and both solutions were cooled for 20 minutes at 0° C. The flask was tilted to start the reaction at 0° C., and kept for 30 minutes at 0° C. The flask could be tilted, after 15 minutes, to permit the stopping solution to be introduced into the sidearm and to allow it to cool. The stopping solution was 1.0M ethylene glycol (5.0 mL). After the 30 minute reaction, the flask was tilted to introduce the stopping solution. It was kept for another hour at 0° C., and then removed from the cooling bath. Distilled water (15.0 mL) was added. The sample was run through a well-washed column (5.0 mL) of Dowex AG1-X8, acetate form, 100–200 mesh, followed by three 5.0 mL washes with water. The sample was rotary evaporated to a small volume (about 3.0 mL) and loaded on a column (1.5×95 cm) of well-washed Sephadex G-10 (40–120 μm bead size), run in water. Fractions containing the oligosaccharide product were pooled. The product was 2-O-(2-acetamido-2-deoxy-β-D-glucopyranosyl)-glycolaldehyde; 90% yield.

E. 2-acetamido-2-deoxy-3-O-(β-D-galactopyranosyl)-D-galactitol (β-D-Galp-(1-3)-D-GalNAcitol)

This reduced oligosaccharide (1.0 μmol) was dissolved in a solution containing 1.0 mL water, 3.0 mL glacial acetic acid, and 9.0 mL methanol. The mixture was placed in the bottom of a flask having a sidearm capable of holding 6.5 mL when tilted (Kontes Glass, article 881675-0125), along with a magnetic stir bar. The flask was lowered into an ethanol bath maintained at −76° C. with solid carbon dioxide, and allowed to cool for 15 minutes. The flask should be stoppered to prevent condensation. Lead tetraacetate (0.5 mmol) was added, and the solution stirred for 1 hour. The flask could be tilted, after 40 minutes, to permit the stopping solution to be introduced into the sidearm and to allow it to cool. The stopping solution was comprised of a mixture of 0.48 mL distilled water, 1.43mL glacial acetic acid, 4.31 mL methanol, and 0.28 mL ethylene glycol. After the 1 hour reaction, the flask was tilted to introduce the stopping solution into the reaction mixture. It was kept for another hour at −76° C., and then removed from the cooling bath. Distilled water (20.0 mL) was added. The solution was loaded on a column (5.0 mL) of Dowex AG50W-X8, H+ form, followed by three 5.0 mL washes of water. The total eluent was rotary evaporated to reduce the volume to about 3.5 mL and loaded on a column (1.5×95 cm) of well-washed Sephadex G-10 (40–120 μm bead size) run in water. Fractions containing the oligosaccharide product were pooled. The product was 3-acetamido-3-deoxy-2-O-(β-D-galactopyranosyl)-L-threose; >90% yield.

F. 2-acetamido-2-deoxy-6-O-(2-acetamido-2-deoxy-β-D-glucopyranosyl)-3-O-(β-D-galactopyranosyl)-D-galactitol (β-D-Galp-(1-3)[β-D-GlcpNAc-(1-6)]-D-GalNAcitol)

This branched, reduced oligosaccharide (up to 5 μmol) was dissolved in 2.5 mL of a solution containing 1:1 (vol/vol) methylsulfoxide (anhydrous, Aldrich) and glacial acetic acid. The solution was placed in the bottom of a flask having a sidearm capable of holding 2.5 mL when tilted (Kontes Glass, article 881675-0125). The flask was lowered into a methanol bath at −40° C., maintained in a Haake-Buchler F3-Q cryostat. A freshly-prepared solution containing 2.5 mmol of lead tetraacetate dissolved in 2.5 mL of 1:1 (vol/vol) methylsulfoxide:glacial acetic acid was introduced into the sidearm of the flask, and both solutions were cooled for 20 minutes at −40° C., stoppering the flask to prevent water condensation. The flask was tilted to start the reaction at −40° C., and kept for 1 h at −40° C. The flask could be tilted, after about 40 minutes, to permit the stopping solution to be introduced into the sidearm and allow it to cool. The stopping solution was comprised of 1.0 mL methylsulfoxide, 1.0 mL glacial acetic acid, and 0.5 mL 2,3-butanediol (Aldrich, product B8,490-4). After the 1 hour reaction, the flask was tilted to introduce the stopping solution into the reaction mixture. It was kept for 1 hour at −40° C., and then distilled water (15 mL) was added. Upon warming to room temperature, the solution was run through a well-washed column (5.0 mL) of Dowex AG50W-X8, H+ form, 100–200 mesh, followed with three 5.0 mL washes with water. The solution was rotary evaporated (35° C.) to remove volatile materials, which was repeated twice after two more additions (20 mL) of water. The sample was then placed under high vacuum (<100 mTorr) overnight. The products were 2-O-(2-acetamido-2-deoxy-β-D-glucopyranosyl)-glycolaldehyde and 3-acetamido-3-deoxy-2-O-(β-D-galactopyranosyl)-L-threose; both >95% yield.

G. 2-acetamido-2-deoxy-4-O-(β-D-galactopyranosyl)-D-glucitol (β-D-Galp-(1-4)-D-GlcNAcitol)

This reduced oligosaccharide (52 μmol) was dissolved in 4.0 mL of a solution containing 1:1 (vol/vol) methylsulfoxide (anhydrous, Aldrich) and glacial acetic acid. The solution was placed in the bottom of a flask having a sidearm capable of holding 6.0 mL when tilted (Kontes Glass, article 881675-0125). The flask was lowered into a methanol bath at −30° C., maintained in a Haake-Buchler F3-Q cryostat. A freshly-prepared solution containing 0.5 mmol of lead tetraacetate dissolved in 6.0 mL of 1:1 (vol/vol) methylsulfoxide:glacial acetic acid was introduced into the sidearm of the flask, and both solutions were cooled for 20 minutes at −30° C., stoppering the flask to prevent water condensation. The flask was tilted to start the reaction at −30° C., and kept for 1 h at −30° C. The flask could be tilted, after about 40 minutes, to permit the stopping solution to be introduced into the sidearm and allow it to cool. The stopping solution was comprised of 1.0 mL methylsulfoxide, 1.0 mL glacial acetic acid, and 0.5 mL 2,3-butanediol (Aldrich, product B8,490-4). After the 1 hour reaction, the flask was tilted to introduce the stopping solution into the reaction mixture. It was kept for 1 hour at −30° C., and then distilled water (15 mL) was added. Upon warming to room temperature, the solution was run through a well-washed column (5.0 mL) of Dowex AG50W-X8, H+ form, 100–200 mesh, followed with three 5.0 mL washes with water. The solution was rotary evaporated (35° C.) to remove volatile materials. The sample was then placed under high vacuum (<100 mTorr) overnight. The product was 4-acetamido-4-deoxy-2-O-(β-D-galactopyranosyl)-L-xylose; >90% yield.

H. 6-O-β-D-glucopyranosyl-D-glucitol (α-D-Glcp-(1-6)-D-glucitol)

This reduced oligosaccharide (46 μmol) was dissolved in 4.0 mL of a solution containing 1:1 (vol/vol) methylsulfoxide (anhydrous, Aldrich) and glacial acetic acid. The solution was placed in the bottom of a flask having a sidearm capable of holding 6.0 mL when tilted (Kontes Glass, article 881675-0125). The flask was lowered into a methanol bath at −30° C., maintained in a Haake-Buchler F3-Q cryostat. A freshly-prepared solution containing 0.5 mmol of lead tetraacetate dissolved in 6.0 mL of 1:1 (vol/vol) methylsulfoxide:glacial acetic acid was introduced into the sidearm of the flask, and both solutions were cooled for 20 minutes at −30° C., stoppering the flask to prevent water condensation. The flask was tilted to start the reaction at −30° C., and kept for 1 h at −30° C. The flask could be tilted, after about 40 minutes, to permit the stopping solution to be introduced into the sidearm and allow it to cool. The stopping solution was comprised of 1.0 mL methylsulfoxide, 1.0 mL glacial acetic acid, and 0.5 mL 2,3-butanediol (Aldrich, product B8,490-4). After the 1 hour reaction, the flask was tilted to introduce the stopping solution into the reaction mixture. It was kept for 1 hour at −30° C., and then distilled water (15 mL) was added. Upon warming to room temperature, the solution was run through a well-washed column (5.0 mL) of Dowex AG50W-X8, H+ form, 100–200 mesh, followed with three 5.0 mL washes with water. The solution was rotary evaporated (35° C.) to remove volatile materials. The sample was then placed under high vacuum (<100 mTorr) overnight. The product was 2-O-(β-D-glucopyranosyl)-glycolaldehyde; >80% yield.

I. 4-O-(6-O-α-D-glucopyranosyl-α-D-glucopyranosyl)-D-glucitol (α-D-Glcp-(1-6)-α-D-Glcp-(1-4)-D-Glcitol)

This reduced oligosaccharide (30 μmol) was dissolved in 4.0 mL of a solution containing 1:1 (vol/vol) methylsulfoxide (anhydrous, Aldrich) and glacial acetic acid. The solution was placed in the bottom of a flask having a sidearm capable of holding 6.0 mL when tilted (Kontes Glass, article 881675-0125). The flask was lowered into a methanol bath at −30° C., maintained in a Haake-Buchler F3-Q cryostat. A freshly-prepared solution containing 0.5 mmol of lead tetraacetate dissolved in 6.0 mL of 1:1 (vol/vol) methylsulfoxide:glacial acetic acid was introduced into the sidearm of the flask, and both solutions were cooled for 20 minutes at −30° C., stoppering the flask to prevent water condensation. The flask was tilted to start the reaction at −30° C., and kept for 1 h at −30° C. The flask could be tilted, after about 40 minutes, to permit the stopping solution to be introduced into the sidearm and allow it to cool. The stopping solution was comprised of 1.0 mL methylsulfoxide, 1.0 mL glacial acetic acid, and 0.5 mL 2,3-butanediol (Aldrich, product B8,490-4). After the 1 hour reaction, the flask was tilted to introduce the stopping solution into the reaction mixture. It was kept for 1 hour at −30° C., and then distilled water (15 mL) was added. Upon warming to room temperature, the solution was run through a well-washed column (5.0 mL) of Dowex AG50W-X8, H+ form, 100–200 mesh, followed with three 5.0 mL washes with water. The solution was rotary evaporated (35° C.) to remove volatile materials. The sample was then placed under high vacuum (<100 mTorr) overnight. The product was 2-O-(6-O-α-D-glucopyranosyl-α-D-glucopyranosyl)-D-erythrose; >90% yield.

J. 2-acetamido-2-deoxy-4-O-(2-acetamido-2-deoxy-β-D-glucopyranosyl)-D-glucitol (β-D-GlcpNAc-(1-4)-D-GlcNAcitol)

This reduced oligosaccharide (0.5 μmol) in 5.0 mL water was cooled to 0° C. A solution containing periodic acid (1.0 mmol) in 5.0 mL water at 0° C. was mixed with the first solution, and kept at 0° C. for 20 minutes. At this point, a solution containing 0.9 mL 2,3-butanediol (Aldrich, product B8,490-4) and 9.1 mL water, cooled to 0° C., was added. The mixture was kept at 0° C. for 1 hour, then brought to room temperature. The solution was run through a well-washed column (5.0 mL) of Dowex AG1-X8, 100–200 mesh, acetate form, followed by three washes with 5.0 mL of water. The sample was rotary evaporated to dryness. The product was 4-acetamido-4-deoxy-2-O-(2-acetamido-2-deoxy-β-D-glucopyranosyl)-L-xylose; 89% yield.

EXAMPLE 3

Cleavage of Oligosaccharides

A. 3-acetamido-3-deoxy-2-O-(β-D-galactopyranosyl)-L-threose (β-D-Galp-(1-2)-L-Threo-3-NAc)

This oligosaccharide (2.0 μmol) was dissolved in 0.5 mL of anhydrous hydrazine (Aldrich) in a small vial (Pierce Reacti-vial, with Tuf-bond Teflon-silicone cap seals). The vial was capped under argon gas. The sample was warmed in a heating block to 55° C. for 20 hours. Hydrazine was removed under vacuum in a Speed-Vac centrifugal concentrator. The sample was analyzed after deprotection, as described below. The product was D-galactose; >90% yield.

B. 3-O-α-D-glucopyranosyl-D-fructose (α-D-Glcp-(1-3)-D-Fru)

This oligosaccharide (2.0 μmol) was dissolved in 0.5 mL of anhydrous hydrazine (Aldrich) in a small vial (Pierce Reacti-vial, with Tuf-bond Teflon-silicone cap seals). The vial was capped under argon gas. The sample was warmed in a heating block to 55° C. for 20 hours. Hydrazine was removed under vacuum in a Speed-Vac centrifugal concentrator. The sample was analyzed after deprotection, as described below. The product was D-glucose; >98% yield.

C. 2-O-(6-O-[2-acetamido-2-deoxy-β-D-glucopyranosyl]-β-D-galactopyranosyl)-D-erythrose (β-D-GlcpNAc-(1-6)-β-D-Galp-(1-2)-D-Eryth)

This oligosaccharide (2.0 μmol) was dissolved in 0.5 mL of anhydrous hydrazine (Aldrich) in a small vial (Pierce Reacti-vial, with Tuf-bond Teflon-silicone cap seals). The vial was capped under argon gas. The sample was warmed in a heating block to 55° C. for 20 hours. Hydrazine was removed under vacuum in a Speed-Vac centrifugal concentrator. The sample was analyzed after deprotection, as described below. The product was 6-O-(2-acetamido-2-deoxy-β-D-glucopyranosyl)-D-galactose; >95% yield.

D. 2-O-β-D-glucopyranosyl-D-glucose (β-D-Glcp-(1-2)-D-Glc)

This oligosaccharide (5.0 μmol) was dissolved in 0.5 mL methylhydrazine (Aldrich) in a small vial (Pierce Reacti-vial, with Tuf-bond Teflon-silicone cap seals). The vial was capped under nitrogen gas. The sample was warmed in a heating block to 70° C. for 24 hours. Methylhydrazine was removed under vacuum in a Speed-Vac centrifugal concentrator. The product was D-glucose methylhydrazone, 50% yield.

E. 2-O-(6-O-α-D-glucopyranosyl-α-D-glucopyranosyl)-D-erythrose (α-D-Glcp-(1-6)-α-D-Glcp-(1-2)-D-Eryth)

This oligosaccharide (5.0 μmol) was dissolved in 0.5 mL of anhydrous hydrazine (Aldrich) in a small vial (Pierce Reacti-vial, with Tuf-bond Teflon-silicone cap seals). The vial was capped under argon gas. The sample was warmed in a heating block to 70° C. for 48 hours. Hydrazine was removed under vacuum in a Speed-Vac centrifugal concentrator. The sample was analyzed after deprotection, as described below. The product was 6-O-α-D-glucopyranosyl-D-glucose; >97%.yield.

F. 2-O-α-D-glucopyranosyl-glycolaldehyde

This oligosaccharide (5.0 μmol) was dissolved in 0.5 mL anhydrous hydrazine (Aldrich) in a small vial (Pierce Reacti-vial, with Tuf-bond Teflon-silicone cap seals). The vial was capped under argon gas. The sample was warmed in a heating block to 70° C. for 24 hours. Hydrazine was removed under vacuum in a Speed-Vac centrifugal concentrator. The sample was analyzed after deprotection, as described below. The product was D-glucose; 80% yield.

G. 2-O-β-D-glucopyranosyl-D-glucose (β-D-Glcp-(1-2)-D-Glc)

This oligosaccharide (5.0 μmol) was dissolved in 0.5 mL methylhydrazine (Aldrich) in a small vial (Pierce Reacti-vial, with Tuf-bond Teflon-silicone cap seals). The vial was capped under nitrogen gas, and kept for 3days at room temperature (~22° C.). Methylhydrazine was removed under vacuum in a Speed-Vac centrifugal concentrator. The product was dissolved in 0.3mL dry N,N-dimethylformamide, and lyophilized to dryness. It was taken up in 0.5 mL dry N,N-dimethylformamide, sealed under nitrogen, and heated at 102° C. for 24 hours. The sample was lyophilized, and analyzed without deprotection. The product was D-glucose (40% yield) and D-glucose methylhydrazone (10% yield).

H. 4-acetamido-4-deoxy-2-O-(β-D-galactopyranosyl)-L-xylose (β-D-Galp-(1-2)-L-Xyl-4-NAc)

This oligosaccharide (2.0 μmol) was dissolved in 0.5 mL anhydrous hydrazine (Aldrich) in a small vial (Pierce Reacti-vial, with Tuf-bond Teflon-silicone cap seals). The vial was capped under argon gas. The sample was warmed in a heating block to 55° C. for 20 hours. Hydrazine was removed under vacuum in a Speed-Vac centrifugal concentrator. The sample was analyzed after deprotection, as described below. The product was D-galactose; >90% yield.

I. 2-O-β-D-glucopyranosyl-D-glucose (β-D-Glcp-(1-2)-D-Glc)

This oligosaccharide (10.0 μmol) along with phenylhydrazine hydrochloride (Aldrich, 10.0 μmol) and sodium acetate (10.0 μmol) were dissolved in 50 μL water in a small vial (Pierce Reacti-vial, with Tuf-bond Teflon silicone cap seals). The vial was capped under nitrogen gas. The sample was warmed in a heating block to 70° C. for 12 hours. The solution gave an orange-yellow precipitate. The precipitate was washed with water (4×100 μL) to give a water-soluble product, and a water-insoluble product. The water-insoluble material was the cleavage product, glucose phenylosazone (D-arabino-hexosulose phenylosazone, 20% yield). A small amount of D-glucose (<5% yield) was present in the water-soluble fraction.

J. 2-O-β-D-glucopyranosyl-D-glucose (β-D-Glcp-(1-2)-D-Glc)

This oligosaccharide (up to 12 μmol) was dissolved in 0.5 mL anhydrous hydrazine (Aldrich) in a small vial (Pierce Reacti-vial, with Tuf-bond Teflon-silicone cap seals). The vial was capped under argon gas. The sample was warmed in a heating block to 55° C. for 20 hours. Hydrazine was removed under vacuum in a Speed-Vac centrifugal concentrator. The sample was analyzed after deprotection, as described below. The product was D-glucose; >95% yield.

K. 2-O-α-D-glucopyranosyl-D-glucose (α-D-Glcp-(1-2)-D-Glc)

This oligosaccharide (up to 12 μmol) was dissolved in 0.5 mL anhydrous hydrazine (Aldrich) in a small vial (Pierce Reacti-vial, with Tuf-bond Teflon-silicone cap seals). The vial was capped under argon gas. The sample was warmed in a heating block to 55° C. for 20 hours. Hydrazine was removed under vacuum in a Speed-Vac centrifugal concentrator. The sample was analyzed after deprotection, as described below. The product was D-glucose; >90% yield.

L. 2-O-β-D-glucopyranosy-D-glucose (β-D-Glcp-(1-2)-D-Glc)

This oligosaccharide (5 μmol), sodium acetate (10 μmol) and p-tolylhydrazine hydrochloride (30 μmol) were dissolved in 0.15 mL water in a small vial (Pierce reacti-vial, 0.2 mL capacity, with Tuf-bond Teflon-silicone cap seals). The vial was sealed under argon and warmed on a heating block to 70° C. for 6 hours; the solution became yellow over time and gave a yellow crystalline precipitate, which increased upon cooling to room temperature overnight. The water-insoluble material was the cleavage product, glucose p-tolylosazone (D-arabino-hexos-2-ulose p-tolylosazone). The water soluble fraction contained 2-O-β-D-glucopyranosyl-D-glucose p-tolylhydrazone, and small amounts of D-glucose and the starting oligosaccharide.

M. 2-O-β-D-glucopyranosyl-D-glucose (β-D-Glcp-(1-2)-D-Glc)

This oligosaccharide (5 μmol), sodium acetate (10 μmol) and o-tolylhydrazine hydrochloride (30 μmol) were dissolved in 0.15 mL water in a small vial (Pierce reacti-vial, 0.2 mL capacity, with Tuf-bond Teflon-silicone cap seals). The vial was sealed under argon and warmed on a heating block to 70° C. for 6 hours; the solution became yellow over time and gave a yellow crystalline precipitate, which increased upon cooling to room temperature overnight. The water-insoluble material was the cleavage product, glucose o-tolylosazone (D-arabino-hexos-2-ulose o-tolylosazone. The water soluble fraction contained 2-Oβ-D-glucopyranosyl-D-glucose o-tolylhydrazone, and small amounts of D-glucose and the starting oligosaccharide.

N. 2-Oβ-D-glucopyranoyl-D-glucose (β-D-Glcp-(1-2)-D-Glc)

To this oligosaccharide (5 μmol), sodium acetate (10 μmol) and 4-fluorophenylhydrazine hydrochloride (5.5 μmol, Aldrich) in a small vial (Pierce reacti-vial, 0.2 mL capacity, with Tuf-bond Teflon-silicone cap seals) was added 100 μL water. The vial was sealed under nitrogen and heated to 70° C. for 24 hours. A water-insoluble product was the cleavage product, glucose 4-fluorophenyl osazone (D-arabino-hexos-2-ulose 4-fluorophenylosazone). The water soluble fraction contained D-glucose and the starting oligosaccharide, in a 1:3 ratio.

O. 2-O-β-D-glucopyranosyl-D-glucose (β-D-Glcp-(1-2)-D-Glc)

To this oligosaccharide (5 μmol), sodium acetate (10 μmol) and 2,4-difluorophenylhydrazine hydrochloride (6.4 μmol, Aldrich) in a small vial (Pierce reacti-vial, 0.2 mL capacity, with Tuf-bond Teflon-silicone cap seals) was added 100 μL water. The vial was sealed under nitrogen and heated to 70° C. for 24 hours. A water-insoluble product was the cleavage product, glucose 2,4-difluorophenylosazone (D-arabino-hexos-2-ulose 2,4-difluorophenylosazone). The water soluble fraction contained D-glucose and the starting oligosaccharide, in a 1:4 ratio.

P. 2-O-β-D-glucopyranosyl-D-glucose (β-D-Glcp-(1-2)-D-Glc)

To this oligosaccharide (10 μmol), sodium acetate (30 μmol) in a small vial (Pierce reacti-vial, 0.2 mL capacity, with Tuf-bond Teflon-silicone cap seals) was added 150 μL water. 3-(trifluoromethyl)phenylhydrazine (40 μmol, Aldrich) was added, the sample sealed under nitrogen, and heated to 90° C. for 48 hours. The oligosaccharide was converted (>98%) to D-glucose and D-glucose 3-(trifluoromethyl)phenyl hydrazone, in a 1:2 ratio.

Q. 2-O-β-D-glucopyranosyl-D-glucose (β-D-Glcp-(1-2)-D-Glc)

To this oligosaccharide (10 μmol), in a small vial (Pierce reacti-vial, 0.2 mL capacity, with Tuf-bond Teflon-silicone cap seals) was added 150 μL of a solution containing 1/1 (W/W) 2-hydrazinopyridine in water. This was capped under nitrogen, and heated to 90° for 48 h. The sample was then taken up in 1.0 mL water and dried under vacuum. The oligosaccharide was converted (>98%) to D-glucose 2-pyridinylhydrazone.

R. 3-O-β-D-galactopyranosy-D-erythro-pentos-2-ulose phenylosazone

This 3-substituted phenylosazone derivative (1.1 mg) was dissolved in 100 μL anhydrous hydrazine, in a small vial (Pierce reacti-vial, 0.2 mL capacity, with Tuf-bond Teflon-silicone cap seals. This was capped under nitrogen, and warmed to 70° C. for 26 h. The hydrazine was removed on a Speed-vac centrifugal concentrator under vacuum. The sample was analyzed after deprotection, as described below. The product was D-galactose (>90% yield).

S. 2-O-α-D-mannopyranosyl-D-mannose (α-D-Manp-(1-2)-D-Man)

To this oligosaccharide (3.0 μmol), in a small vial (Pierce reacti-vial with Tuf-bond Teflon-silicone cap seals) was added 0.5 mL of anhydrous hydrazine (Aldrich). The vial was capped under argon gas. The sample was warmed to 65° C. for 48 hours. Hydrazine was removed under vacuum in a Speed-Vat centrifugal concentrator. The sample was analyzed after deprotection, as described below. The product was D-mannose; 88% yield.

EXAMPLE 4

Deprotection Following Cleavage of Oligosaccharides

A. D-glucose hydrazone

D-glucose hydrazone (up to 12 μmol) from B, F, J and K of Example 3 was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex–AG50W-X8, H+ form, 100–200 mesh, and Dowex AG1-X8, acetate form, 100–200 mesh. The columns were washed with four additional 5.0 mL volumes of water. The total eluent was rotary evaporated to dryness. The product was D-glucose; >99% deprotected.

B. 6-O-α-D-glucopyranosyl-D-glucose hydrazone

This oligosaccharide (5 μmol) from E of Example 3 was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 6-O-α-D-glucopyranosyl-D-glucose; >99% deprotected.

C. 3-O-α-D-mannopyranosyl-D-mannose hydrazone

This oligosaccharide (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 3-O-α-D-mannopyranosyl-D-mannose; >99% deprotected.

D. 6-O-(2-acetamido-2-deoxy-β-D-glucopyranosyl)-D-galactose hydrazone

This oligosaccharide (2.0 μmol) from C of Example 3 was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve, and the solution was kept at room temperature for 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 6-O-(2-acetamido-2-deoxy-β-D-glucopyranosyl)-D-galactose; >99% deprotected.

E. D-galactose hydrazone

D-galactose hydrazone (up to 10 μmol) from A, H and R of Example 3 was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-galactose; >99% deprotected.

F. 4-O-β-galactopyranosyl-D-glucose hydrazone

This oligosaccharide (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 4-O-β-galactopyranosyl-D-glucose; >98% deprotected.

G. D-mannose hydrazone

D-mannose hydrazone (10 μmol) was dissolved in 1.0 mL of a solution saturated in sodium bicarbonate. Acetic anhydride (50 μL) was added, with gently swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-mannose; >98% deprotected.

H. 2-acetamido-2-deoxy-D-glucose hydrazone 2-acetamido-2-deoxy-D-glucose hydrazone (10 µmol) was dissolved in 1.0 mL of a solution saturated in sodium bicarbonate. Acetic anhydride (50 µL) was added, with gentle swirling at room temperature to dissolve it. After 10 minutes, another 50 µL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 2-acetamido-2-deoxy-D-glucose; >97% deprotected.

I. 4-O-α-D-glucopyranosyl-D-glucose hydrazone

This oligosaccharide (5 µmol) was dissolved in 1.0mL of a solution saturated in sodium bicarbonate. Acetic anhydride (50 µL) was added, with gently swirling at room temperature to dissolve it. After 10 minutes, another 50 µL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 4-O-α-D-glucopyranosyl-D-glucose; >98% deprotected.

J. 3-O-β-D-galactopyranosyl-D-arabinose hydrazone

This oligosaccharide (5 µmol) was dissolved in 1.0 mL of a solution saturated in sodium bicarbonate. Acetic anhydride (50 µL) was added, with gentle swirling at room temperature to dissolve it. After 10 minutes, another 50 µL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 3-O-β-D-galactopyranosyl-D-arabinose; >98% deprotected.

K. 2-O-β-D-glucopyranosyl-D-glucose hydrazone

This oligosaccharide (5 µmol) was dissolved in 1.0 mL of a solution saturated in sodium bicarbonate. Acetic anhydride (50 µL) was added, with gentle swirling at room temperature to dissolve it. After 10 minutes, another 50 µL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 2-O-β-D-glucopyranosyl-D-glucose; >98% deprotected.

L. 2-acetamido-2-deoxy-D-galactose hydrazone 2-acetamido-2-deoxy-D-galactose hydrazone (10 µmol) was dissolved in 1.0 mL of a solution saturated in sodium bicarbonate. Acetic anhydride (50 µL) was added, with gentle swirling at room temperature to dissolve it. After 10 minutes, another 50 µL of acetic anhydride was added, gently swirled to dissolve, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 2-acetamido-2-deoxy-D-galactose; >98% deprotected.

M. 6-deoxy-L-galactose hydrazone (L-fucose hydrazone)

6-deoxy-L-galactose hydrazone (L-fucose hydrazone) was dissolved in 1.0 mL of a solution saturated in sodium bicarbonate. Acetic anhydride (50 µL) was added, with gentle swirling at room temperature to dissolve it. After 10 minutes, another 50 µL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was 6-deoxy-L-galactose; >98% deprotected.

N. D-allose hydrazone

D-allose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-allose; >98% deprotected.

O. D-altrose hydrazone

D-altrose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-altrose; >98% deprotected.

P. D-gulose hydrazone

D-gulose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-gulose; >98% deprotected.

Q. D-talose hydrazone

D-talose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-talose; >98% deprotected.

R. D-arabinose hydrazone

D-arabinose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-arabinose; >98% deprotected.

S. D-xylose hydrazone

D-xylose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-xylose; >98% deprotected.

T. D-lyxose hydrazone

D-lyxose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-lyxose; >98% deprotected.

U. D-ribose hydrazone

D-ribose hydrazone (10 μmol) was dissolved in 1.0 mL of a solution saturated in sodium bicarbonate. Acetic anhydride (50 μL) was added, with gentle swirling at room temperature to dissolve it. After 10 minutes, another 50 μL of acetic anhydride was added, gently swirled to dissolve it, and the solution was kept at room temperature for another 50 minutes. The sample was diluted with 4.0 mL water, and passed through a 5.0 mL column of Dowex AG50W-X8, H+ form, 100–200 mesh. The column was washed with four 5.0 mL additions of water. The total eluent was rotary evaporated to dryness, taken up in 1.0 mL water, and 1.0 mL of a solution containing 0.2M HCl was added. The solution was incubated at 35° C. for 1 hour. The sample was diluted with 3.0 mL water, and passed, in tandem, through columns of Dowex AG50W-X8, H+ form, 100–200 mesh, and Dowex AG1-X8, acetate form, 100–200 mesh. The columns were washed with an additional four 5.0 mL volumes of water. The total eluent was rotary evaporated to dryness. The product was D-ribose; >98% deprotected.

From the foregoing, it will be appreciated that, although specific embodiments of the invention have been described herein for purposes of illustration, various modifications may be made without deviating from the spirit and scope of the invention.

I claim:

1. A method for the sequential removal of monosaccharides from the reducing end of an oligosaccharide, comprising the steps of:
   (a) generating from the monosaccharide at the reducing end of an oligosaccharide an aldehydo group or keto group on a carbon bonded to the carbon having the glycosidic linkage to an adjacent monosaccharide of said oligosaccharide, without introducing an aldehydo group or keto group on a ring carbon of any other monosaccharide of said oligosaccharide; and
   (b) cleaving the glycosidic bond between the former reducing end monosaccharide and said adjacent monosaccharide of said oligosaccharide using a hydrazine, thereby completing the removal of said former reducing end monosaccharide.

2. The method of claim 1 wherein steps (a) and (b) are repeated on the oligosaccharide.

3. A method for the sequential removal of monosaccharides from the reducing end of an oligosaccharide, comprising the steps of:
   (a) generating from the monosaccharide at the reducing end of an oligosaccharide an aldehydo group or keto group on a carbon bonded to the carbon having the glycosidic linkage to an adjacent monosaccharide of said oligosaccharide, without introducing an aldehydo group or keto group on a ring carbon of any other monosaccharide of said oligosaccharide;
   (b) cleaving the glycosidic bond between the former reducing end monosaccharide and said adjacent monosaccharide of said oligosaccharide using a hydrazine, thereby completing the removal of said former reducing end monosaccharide; and
   (c) converting said former adjacent monosaccharide to a free reducing monosaccharide.

4. The method of claim 3 wherein steps (a) to (c) are repeated on the oligosaccharide.

5. A method for the sequential removal of monosaccharides from the reducing end of an oligosaccharide, comprising the steps of:
   (a) reducing to an alcohol the aldehydo group or keto group of the open-chain form of the monosaccharide at the reducing end of an oligosaccharide without reducing any other functional groups of said oligosaccharide;
   (b) oxidizing vicinal diols of said monosaccharide at the former reducing end of said oligosaccharide without oxidizing vicinal diols or individual hydroxyl groups attached directly to ring carbons of said oligosaccharide, thereby generating from said monosaccharide an aldehydo group or keto group on a carbon bonded to the carbon having the glycosidic linkage to an adjacent monosaccharide of said oligosaccharide; and
   (c) cleaving the glycosidic bond between the former reducing end monosaccharide and said adjacent monosaccharide of said oligosaccharide using a hydrazine, thereby completing the removal of said former reducing end monosaccharide.

6. The method of claim 5 wherein steps (a) to (c) are repeated on the oligosaccharide.

7. A method for the sequential removal of monosaccharides from the reducing end of an oligosaccharide, comprising the steps of:
   (a) reducing to an alcohol the aldehydo group or keto group of the open-chain form of the monosaccharide at the reducing end of an oligosaccharide without reducing any other functional groups of said oligosaccharide;
   (b) oxidizing vicinal diols of said monosaccharide at the former reducing end of said oligosaccharide without oxidizing vicinal diols or individual hydroxyl groups attached directly to ring carbons of said oligosaccharide, thereby generating from said monosaccharide an aldehydo group or keto group on a carbon bonded to the carbon having the glycosidic linkage to an adjacent monosaccharide of said oligosaccharide;

(c) cleaving the glycosidic bond between the former reducing end monosaccharide and said adjacent monosaccharide of said oligosaccharide using a hydrazine, thereby completing the removal of said former reducing end monosaccharide; and (d) converting said former adjacent monosaccharide to a free reducing monosaccharide.

8. The method of claim 7 wherein steps (a) to (d) are repeated on the oligosaccharide.

9. A method for the structural determination of an oligosaccharide, comprising the steps of:

(a) identifying the monosaccharide at the reducing end of an oligosaccharide;

(b) determining the linkage between said reducing end monosaccharide and an adjacent monosaccharide;

(c) generating from the monosaccharide at the reducing end of an oligosaccharide an aldehydo group or keto group on a carbon bonded to the carbon having the glycosidic linkage to an adjacent monosaccharide of said oligosaccharide, without introducing an aldehydo group or keto group on a ring carbon of any other monosaccharide of said oligosaccharide;

(d) cleaving the glycosidic bond between the former reducing end monosaccharide and said adjacent monosaccharide of said oligosaccharide using a hydrazine, thereby completing the removal of said former reducing end monosaccharide; and (e) repeating steps (a) to (d).

10. A method for the structural determination of an oligosaccharide, comprising the steps of:

(a) identifying the monosaccharide at the reducing end of an oligosaccharide;

(b) determining the linkage between said reducing end monosaccharide and an adjacent monosaccharide;

(c) generating from the monosaccharide at the reducing end of an oligosaccharide an aldehydo group or keto group on a carbon bonded to the carbon having the glycosidic linkage to an adjacent monosaccharide of said oligosaccharide, without introducing an aldehydo group or keto group on a ring carbon of any other monosaccharide of said oligosaccharide;

(d) cleaving the glycosidic bond between the former reducing end monosaccharide and said adjacent monosaccharide of said oligosaccharide using a hydrazine, thereby completing the removal of said former reducing end monosaccharide;

(e) converting said former adjacent monosaccharide to a free reducing monosaccharide; and (f) repeating steps (a) to (e).

11. A method for the structural determination of an oligosaccharide, comprising the steps of:

(a) identifying the monosaccharide at the reducing end of an oligosaccharide;

(b) determining the linkage between said reducing end monosaccharide and an adjacent monosaccharide;

(c) reducing to an alcohol the aldehydo group or keto group of the open-chain form of the monosaccharide at the reducing end of said oligosaccharide without reducing any other functional groups on said oligosaccharide;

(d) oxidizing vicinal diols of said monosaccharide at the former reducing end of said oligosaccharide without oxidizing vicinal diols or individual hydroxyl groups attached directly to ring carbons of said oligosaccharide, thereby generating from said monosaccharide an aldehydo group or keto group on a carbon bonded to the carbon having the glycosidic linkage to an adjacent monosaccharide of said oligosaccharide;

(e) cleaving the glycosidic bond between the former reducing end monosaccharide and said adjacent monosaccharide of said oligosaccharide using a hydrazine, thereby completing the removal of said former reducing end monosaccharide; and (f) repeating steps (a) to (e).

12. A method for the structural determination of an oligosaccharide, comprising the steps of:

(a) identifying the monosaccharide at the reducing end of an oligosaccharide;

(b) determining the linkage between said reducing end monosaccharide and an adjacent monosaccharide;

(c) reducing to an alcohol the aldehydo group or keto group of the open-chain form of the monosaccharide at the reducing end of said oligosaccharide without reducing any other functional groups on said oligosaccharide;

(d) oxidizing vicinal diols of said monosaccharide at the former reducing end of said oligosaccharide without oxidizing vicinal diols or individual hydroxyl groups attached directly to ring carbons of said oligosaccharide, thereby generating from said monosaccharide an aldehydo group or keto group on a carbon bonded to the carbon having the glycosidic linkage to an adjacent monosaccharide of said oligosaccharide;

(e) cleaving the glycosidic bond between the former reducing end monosaccharide and said adjacent monosaccharide of said oligosaccharide using a hydrazine, thereby completing the removal of said former reducing end monosaccharide;

(f) converting said former adjacent monosaccharide to a free reducing monosaccharide; and (g) repeating steps (a) to (f).

13. A method for the cleavage of a glycosidic bond, comprising reacting a hydrazine with a compound having the following formula:

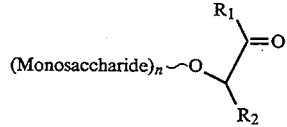

wherein the glycosidic bond between monosaccharide and O is $\alpha$ or $\beta$, n is 1 or more, and $R_1$ and $R_2$ are independently selected from H or an aliphatic group having from 1 to 8 carbon atoms with or without hydroxyl groups and with or without amino groups.

14. The method of claim 13 with an additional second step of converting to a free reducing monosaccharide the monosaccharide formerly bonded directly to O.

* * * * *